United States Patent [19]

Katano et al.

[11] Patent Number: 5,200,407
[45] Date of Patent: Apr. 6, 1993

[54] AZOLE DERIVATIVES AND ANTI-ULCERATIVE COMPOSITION CONTAINING SAME

[75] Inventors: Kiyoaki Katano; Tamako Tomomoto; Hiroko Ogino; Naoki Yamazaki; Fumiya Hirano; Yasukatsu Yuda; Fukio Konno; Motohiro Nishio; Tomoya Machinami; Seiji Shibahara; Takashi Tsuruoka; Shigeharu Inouye, all of Yokohama, Japan

[73] Assignee: Meiji Seika Kaburhiki Kaisha, Yokohama, Japan

[21] Appl. No.: 716,621

[22] Filed: Jun. 14, 1991

Related U.S. Application Data

[62] Division of Ser. No. 544,671, Jun. 27, 1990, Pat. No. 5,079,255.

[30] Foreign Application Priority Data

Jun. 29, 1989 [JP] Japan ................... 1-165244
Nov. 24, 1989 [JP] Japan ................... 1-303366

[51] Int. Cl.$^5$ ................... A61K 31/435; C07D 513/04
[52] U.S. Cl. ................... 514/234.2; 514/253; 514/301; 544/127; 544/362; 546/114
[58] Field of Search ................... 546/114; 544/127, 362; 514/234.2, 253, 301

[56] References Cited

U.S. PATENT DOCUMENTS

| | | | |
|---|---|---|---|
| 4,275,065 | 6/1981 | Wei et al. | 424/256 |
| 4,443,606 | 4/1984 | Wei et al. | 546/114 |
| 4,808,596 | 2/1989 | Matsuishi et al. | 514/303 |
| 4,847,264 | 7/1989 | Campbell et al. | 546/114 |
| 4,880,815 | 11/1989 | Uchida et al. | 514/303 |

FOREIGN PATENT DOCUMENTS

| | | |
|---|---|---|
| 0151826 | 8/1985 | European Pat. Off. |
| 0178438 | 4/1986 | European Pat. Off. |
| 0234690 | 9/1987 | European Pat. Off. |
| 0370436 | 5/1990 | European Pat. Off. |
| 2241575 | 3/1973 | Fed. Rep. of Germany |
| 2190426 | 3/1974 | France |
| 58-116489 | 7/1983 | Japan |
| WO 87/05021 | 8/1987 | PCT Int'l Appl. |

OTHER PUBLICATIONS

Barlin et al., Australian J. Chem., 37, pp. 1729-1737 (1984).
Gayral et al., Eur. J. Med. Chem.-Chim. Ther. 13(2), pp. 171-175 (1978); Chem. Abstracts, vol. 89, 109204h (1978).
Ozawa, Kyoto Daigaku Kekkaku-Kenkyusho Nempo 4, pp. 265-271 (1956); Chem. Abstracts, vol. 51, 5898 gh (1957).
Takahishi et al., Pharm. Bull. (Japan) 4, pp. 20-24 (1956); Chem. Abstracts, vol. 51, 2741i to 2742g (1957).
Takahashi et al., Chem. Abstracts, vol. 51, p. 6634a (1957).
Czarnocka-Janowicz et al., Chem. Abstracts, vol. 94, p. 717 Abstract No. 65548v (1981).
Czarnocka-Janowicz et al., Chem. Abstracts, vol. 99, p. 609 Abstract No. 158326q (1983).

*Primary Examiner*—Bernard Dentz
*Attorney, Agent, or Firm*—Wenderoth, Lind & Ponack

[57] ABSTRACT

Compounds of the general formula (I):

$$R^1 \text{—} \begin{matrix} B \overset{A}{=} \\ C \underset{D}{=} \end{matrix} \begin{matrix} N \\ X \end{matrix} \text{—} (CH_2)_m S \overset{(O)_n}{\longrightarrow} Y \text{—} R^2 \quad (I)$$

and pharmaceutically acceptable salts thereof, in which A, B, C and D each represent —CH= or —N=, with the proviso that at least one of them is —N=;
X represents —NH—, —O— or —S—;
Y represents —(CH$_2$)$_p$— wherein p is an integer from 0 to 4, —C(CH$_3$)$_2$—, —CH$_2$CH=CH—, —CH$_2$CO—, —CF$_2$— or —CH$_2$COCH$_2$—;
R$^1$ represents a hydrogen atom, a C$_{1-4}$ alkyl group, a halogen atom or a C$_{1-4}$ alkoxy group;
R$^2$ represents a hydrogen atom, a hydroxyl group, a saturated or unsaturated C$_{1-6}$ alkyl group, a C$_{1-6}$ alkoxy group, a carboxyl group, a saturated or unsaturated C$_{1-12}$ alkoxycarbonyl group which may be optionally substituted, a cycloalkoxycarbonyl group, a saturated or unsaturated five- or six-membered heterocyclic group containing at least one nitrogen atom optionally with one or more nitrogen and/or oxygen atoms, which may be optionally condensed and/or substituted, $-CONR^3R^4$, $-NR^3R^4$, $-OCOR^3$ or $-NHCONHR^3$ wherein $R^3$ and $R^4$, which may be the same or different, represent a $C_{1-6}$ alkyl group which may be optionally substituted or a cycloalkyl group, and m and n each represent an integer from 0 to 2.

5 Claims, No Drawings

AZOLE DERIVATIVES AND ANTI-ULCERATIVE COMPOSITION CONTAINING SAME

This application is a division of application Ser. No. 544,671, filed Jun. 27, 1990 now U.S. Pat. No. 5,079,255.

BACKGROUND OF THE INVENTION

1. Field of the Invention

The invention relates to azole derivatives having an anti-ulcerative activity and anti-ulcerative compositions containing at least one such azole derivative as an active ingredient.

2. Description of the Related Art

Agents which are effective for both inhibiting the secretion of gastric acid and protecting the gastrointestinal mucosa have been demanded as anti-ulcerative compositions.

As agents for inhibiting the secretion of gastric acid, there have been known histamine $H_2$-receptor antagonist typically represented by cimetidine. They are, however, ineffective for protecting the gastrointestinal mucosa. Because of their side effects upon the central nervous system, they are also less than satisfactory in their applicability to prevention or treatment of ulcers.

$[H^+-K^+]$ ATPase inhibitors typically represented by Omeprazole are strongly effective for inhibiting the secretion of gastric acid, but are known to induce achlorhydria. Another disadvantage of such inhibitors is that they are so unstable to acids that they are likely to be decomposed by gastric acid.

It is thus desired to develop anti-ulcerative agents which not only have a well-balanced effect of both inhibiting the secretion of gastric acid and protecting the gastrointestinal mucosae, but are also efficacious against various ulcers, low toxic and stable to the acid.

We have found that benzothiazole and benzimidazole derivatives have an anti-ulcerative activity (e.g. Japanese Patent Application Ser. No. 293689/88). As a result of further studies, we have now found that some azole derivatives are very efficacious against various, experimentally-induced ulcers, and possess both a strong effect of inhibiting the secretion of gastric acid and an enhanced effect on protecting the gastrointestinal mucosae.

SUMMARY OF THE INVENTION

It is an object of the present invention to provide novel compounds which not only have a well-balanced effect of inhibiting the secretion of gastric acid and protecting the gastrointestinal mucosae but are also efficacious for preventing or treating ulcers, low toxic and stable to the acid.

Thus, one aspect of the invention provides a novel compound having the formula (I):

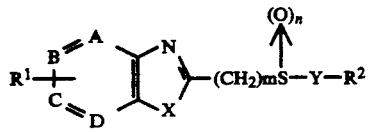

and pharmaceutically acceptable salts thereof, in which A, B, C and D each represent $-CH=$ or $-N=$, with the proviso that at least one of them is $-N=$;

X represents $-NH-$, $-O-$ or $-S-$;

Y represents $-(CH_2)_p-$ wherein p is an integer from 0 to 4, $-C(CH_3)_2-$, $-CH_2CH=CH-$, $-CH_2CO-$, $-CF_2-$ or $-CH_2COCH_2-$;

$R^1$ represents a hydrogen atom, a $C_{1-4}$ alkyl group which may be optionally substituted, a halogen atom or a $C_{1-4}$ alkoxy group which may be optionally substituted;

$R^2$ represents a hydrogen atom, a hydroxyl group, a saturated or unsaturated $C_{1-6}$ alkyl group which may be optionally substituted, $C_{1-6}$ alkoxy group which may be optionally substituted, a carboxyl group, a saturated or unsaturated $C_{1-12}$ alkoxycarbonyl group which may be; optionally substituted, a cycloalkoxycarbonyl group, a saturated or unsaturated five- or six-membered heterocyclic group containing at least one nitrogen atom optionally with one or more nitrogen and/or oxygen atoms, which may be optionally condensed and/or substituted, $-CONR^3R^4$, $-NR^3R^4$, $-OCOR^3$ or $-NH-CONHR^3$ wherein $R^3$ and $R^4$, which may be the same or different, represents a hydrogen atom, a $C_{1-6}$ alkyl group which may be optionally substituted or a cycloalkyl group, and m and n each represent an integer from 0 to 2.

Compounds of formula (I), which have a well-balanced effect of inhibiting the secretion of gastric acid and protecting the gastrointestinal mucosae, are useful in the treatment of ulcerative condition. Accordingly, another aspect of the invention provides a pharmaceutical composition which comprises at least one compound selected from compounds of the general formula (I) and their pharmaceutically acceptable salt.

DETAILED DESCRIPTION

Compounds

The compounds according to the present invention are represented by the above-mentioned formula (I).

In the compounds of formula (I), A, B, C and D each represent $-CH=$ or $-N=$, with the proviso that at least one of them is $-N=$. One preferred group of the compound of formula (I) is that in which one or two of A, B, C and D are $-N=$. If two $-N=$ exist, then they are preferably found in A and D, B and C or B and D.

In the compounds of formula (I), X represents NH, an oxygen atom or a sulfur atom.

Thus, the compounds of formula (I) according to the present invention have a structure in which a pyridine or azine ring is condensed to an azole ring as basic skeleton or framework, for example, thiazolopyridine, thiazolopyridazine, oxazolopyridine or imidazopyridine skeleton.

In the compounds of formula (I), Y represents $-(CH_2)_p-$ wherein p is an integer from 0 to 4, $-C(CH_3)_2-$, $-CH_2CH=CH-$, $-CH_2CO-$, $-CF_2-$ or $-CH_2COCH_2-$.

In the compounds of formula (I), $R^1$ represents a hydrogen atom; a substituted or unsubstituted $C_{1-4}$ alkyl group which may be, for example, methyl, ethyl, n-propyl, isopropyl, n-butyl, isobutyl, t-butyl, trifluoromethyl, 2,2,2-trifluoroethyl, methoxymethyl and ethoxyethyl; a halogen atom such as chlorine and bromine; and a substituted or unsubstituted $C_{1-4}$ alkoxy group which may be, for example, methoxy, ethoxy, n-propoxy, isopropoxy, n-butoxy, isobutoxy, t-butoxy and 2,2,2-trifluoroethoxy. One preferred group of compound of formula (I) is that in which $R^1$ is a chlorine atom at the position B or a trifluoromethyl group at the position C.

In the compounds of formula (I), $R^2$ represents (a) a hydrogen atom, (b) a hydroxyl group, (c) a saturated or unsaturated $C_{1-6}$ alkyl group which may be substituted, (d) a $C_{1-6}$ alkoxy group which may be substituted, (e) a carboxyl group, (f) a saturated or unsaturated $C_{1-12}$ alkoxycarbonyl group which may be substituted, (g) a cycloalkoxycarbonyl group, (h) a saturated or unsaturated five- or six-membered heterocyclic group containing at least one nitrogen atom optionally with one or more nitrogen and/or oxygen atoms, which may be condensed and/or substituted, (i) —$CONR^3R^4$ wherein $R^3$ and $R^4$, which may be the same or different, each represent a hydrogen atom, a $C_{1-6}$ alkyl group which may be substituted or a cycloalkyl group, (j) —$NR^3R^4$ wherein $R^3$ and $R^4$ are each as defined above, (k) —O-$COR^3$ wherein $R^3$ is as defined above, and (l) —NH-$CONHR^3$ wherein $R^3$ is as defined above.

The saturated or unsaturated $C_{1-6}$ alkyl group (c), may be a straight chain or branched chain alkyl group, for example, methyl, ethyl, propyl, isopropyl, n-butyl, isobutyl, t-butyl, n-pentyl, vinyl, 2-methyl-1-propenyl and 3-methyl-2-butenyl.

The $C_{1-6}$ alkoxy group (d), of which the alkyl moiety may be a straight chain or branched chain alkyl group, may be, for example, methoxy, ethoxy, n-propoxy, isopropoxy, n-butoxy, isobutoxy, t-butoxy, n-pentoxy, isopentoxy and hexyloxy.

The saturated or unsaturated $C_{1-12}$ alkoxycarbonyl group (f), of which the alkyl moiety may be a straight chain or branched chain alkyl group, may be, for example, methoxycarbonyl, ethoxycarbonyl, n-propoxycarbonyl, isopropoxycarbonyl, n-butoxycarbonyl, isobutoxycarbonyl, t-butoxycarbonyl, n-pentoxycarbonyl, isopentoxycarbonyl, hexyloxycarbonyl, octoxycarbonyl, vinyloxycarbonyl, allyloxycarbonyl, 1-propenyloxycarbonyl, 1-butenyloxycarbonyl, crotyloxycarbonyl, geranyloxycarbonyl and 6,7-epoxygeranyloxycarbonyl.

The cycloalkoxycarbgnyl group (g) may be, for example, cyclopentyloxycarbonyl and cyclohexyloxycarbonyl.

The heterocyclic group (h) is a five- or six-membered ring containing at least one nitrogen atom optionally with one or more nitrogen and/or oxygen atoms, which may be either saturated or unsaturated, may be substituted by a substituent and may be condensed with other ring. The group (h) may be, for example, 1-pyrrolidinyl, 2-pyrrolidinyl, 3-pyrrolidinyl, 2-(1-methyl)pyrrolidinyl, 3-(1-methyl)pyrrolidinyl, 2-(1-ethyl)pyrrolidinyl, 3-(1-ethyl)pyrrolidinyl, 1-piperazinyl, 1-(4-methyl)piperazinyl, 1-piperidinyl, 2-(1-methyl)piperidinyl, 3-(1-methyl)piperidinyl, 4-(1-methyl)piperidinyl, 2,6-dimethyl-1-piperidinyl, 2,2,6,6-tetramethyl-1-piperidinyl, 2-pyridinyl, 3-pyridinyl, 4-pyridinyl, 2-oxazolidinon-5-yl, morpholinyl, 1-methyltetrazol-5-yl, 1-cyclohexyltetrazol-5-yl, 1,3-dioxoisoindol-2-yl and 4-methylimidazol-5-yl.

In the groups (i) —$CONR^3R^4$, (j) —$NR^3R^4$, (k) —O-$COR^3$ and (l) —$NHCONHR^3$, $R^3$ and $R^4$ each represent a hydrogen atom, a $C_{1-6}$ alkyl group such as methyl, ethyl, n-propyl, isopropyl, n-butyl, isobutyl, t-butyl, pentyl, hexyl, 2,2,2-trifluoroethyl, or a cycloalkyl group such as cyclohexyl and cyclopentyl groups.

The compounds of formula (I) may exist in the form of their salts resulting from the basicity of the thiazole or pyridine ring moiety which may be found in their skeletons, the acidity of the substituents, and so on. With the use of salts in mind, pharmaceutically acceptable salts are preferred. Suitable pharmaceutically acceptable salts of the compounds of formula (I) include acid salts such as hydrochlorides, hydrobromides, acetates, succinates and lactates; basic salts with suitable bases such as sodium, potassium, calcium, ammonium, triethylamine and ethanolamine; and amino acid salts with a suitable amino acid such as lysine, arginine and aspartic acid.

It will be appreciated that the compounds of formula (I) have asymmetric carbon or sulfur atoms, and all optical and geometric isomers of compounds of formula (I) are embraced by the invention.

Preparation of the Compounds

The compounds of formula (I) according to the present invention are primarily characterized in that the skeleton in which a pyridine or azine ring is condensed to an azole ring has a substituent containing a sulfur atom, a sulfinyl or sulfonyl group, optionally with a substituent being included in the pyridine or azine ring.

The compounds of formula (I) according to the present invention may be synthesized by any method suitable or reasonable in respect of the formation of the above basic skeleton and formation and introduction of the substituents.

The compounds of formula (I) and pharmaceutically acceptable salts thereof may be prepared by the general methods outlined hereinafter.

(1) The compounds of the formula (I) wherein n =0 may be prepared by either one of the following processes (A) and (B).

According to a first general process (A), a compound of formula (I) wherein n=0 may be prepared by reacting a compound of the general formula (II):

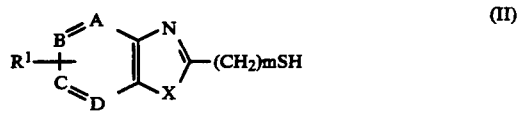

(II)

wherein A, B, C, D, X, $R^1$ and m are as previously defined, with a compound having the general formula (III):

Z—$YR^2$ (III)

wherein Y and $R^2$ are as previously defined, and Z is a halogen atom or a tosyloxy, trifluoromethanesulfonyloxy or mesyloxy group, in the presence of sodium hydrogencarbonate, potassium hydrogencarbonate, potassium carbonate, sodium carbonate, sodium hydroxide, potassium hydroxide or a metal hydride (e.g., sodium hydride, potassium hydride or the like), at a temperature of from −30° to 150° C., preferably 10° to 100° C. for 30 minutes to 24 hours in an inert solvent, such as N,N-dimethylformamide, dioxane, tetrahydrofuran, water or ethanol.

According to another general process (B), a compound of formula (I) wherein n=0, may be prepared by reacting a compound of the general formula (IV):

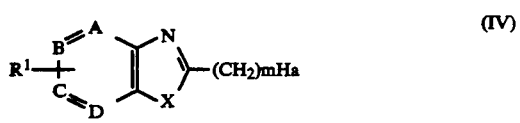

(IV)

wherein A, B, C, D, X, $R^1$ and m are as previously defined and Ha represents a halogen atom such as chlorine, bromine and iodine, with a compound having the general formula (V):

HS—YR[2]     (V)

wherein Y and R[2] are as previously defined, in the presence of sodium hydrogencarbonate, potassium hydrogencarbonate, potassium carbonate, sodium carbonate, sodium hydroxide, potassium hydroxide or a metal hydride (e.g., sodium hydride, potassium hydride or the like), at a reaction temperature of from −30° to 150° C., preferably 10° to 100° C., for 30 minutes to 24 hours in an inert solvent, such as N,N-dimethylformamide, dioxane, tetrahydrofuran, water or ethanol.

(2) The compounds of formula (I) wherein n=1 may be obtained by reacting the compound of the general formula (I) wherein n=0 obtained as above with 1 to 1.2 equivalents of an oxidizing agent in an inert solvent. If the amount of the oxidizing agent is increased to 2 to 3 equivalents in the oxidizing reaction, then it is possible to obtain sulfone compounds having the general formula (I) wherein n=2.

The oxidizing agents used in such oxidizing reactions may include hydrogen peroxide, metachloroperbenzoic acid, tert-butyl hydroperoxide, N-bromosuccinimide, manganese dioxide or the like. The solvents used may be conventional ones, including water, acetic acid, a halogenated alkyl such as methylene chloride, ketones such as acetone or the like. Preferably, the oxidizing reactions may be carried out using hydrogen peroxide in the presence of sodium tungstate in acetic acid or using metachloroperbenzoic acid in methylene chloride.

(3) The compounds of the above general formula (II) may be obtained by reacting a compound of the general formula (VI):

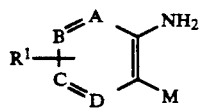     (VI)

wherein A, B, C, D, and R[1] are as previously defined, and M is a halogen atom or an SH group, with carbon disulfide, thiophosgene, potassium methoxanthogenic acid or the like, in an inert solvent such as N,Ndimethylformamide, methanol, ethanol, ethylene glycol monomethyl ether, dioxane or the like), optionally, in the presence of a base (e.g. potassium hydroxide, sodium hydroxide, sodium, potassium carbonate, triethylamine, diisopropylamine or the like).

One example of the process for preparing the compounds of the formula (IV) is known (e.g. Japanese Patent Laid-Open Publication No. 114988/87).

Use of the Compounds/Anti-ulcerative Composition

The compounds of formula (I), which have a well-balanced effect of inhibiting the secretion of gastric acid and protecting the gastrointestinal mucosae, are useful in the prevention or treatment of ulcerative conditions.

The compound of formula (I) or salts thereof may be administered as the raw material, but the active ingredient is preferably presented as a pharmaceutical formulation. The compound may be mixed with pharmaceutically acceptable carriers, vehicles and diluents, and may be formulated for oral or parenteral administration. A suitable daily dose of the compound for oral administration to man is 50 to 500 mg. Formulation for parenteral administration by injection may be obtained as an aqueous solution in which a pharmaceutically acceptable, water-soluble salt of the compound is dissolved in water at a concentration of 0.5 to 10% by weight. A suitable dose for administration by injection to man is 0.5 to 10 mg/day.

While the invention is further illustrated by the following Examples, it should be understood that the invention is not limited to the specific examples.

EXAMPLE 1

2-[(n-butoxycarbonylmethyl)thio]thiazolo[5,4-b]pyridine

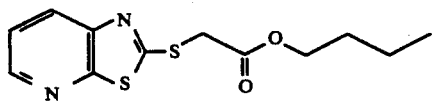

Twenty-four (24) g of 2-mercaptothiazolo[5,4-b]pyridine was dissolved in 300 ml of N,Ndimethylformamide, and 43.3 g of potassium carbonate and 23.65 g of chloroacetic acid n-butyl ester were added to the solution, followed by one-hour stirring at room temperature. Seven hundred (700) ml of ethyl acetate was added to the solution, which was then washed with water three times, dehydrated over magnesium sulfate, dried and distilled to remove the solvent to obtain the title compound (39.9 g, 99%).

$^1$HNMR(CDCl$_3$) δ:
0.89 (3H, t), 1.36 (2H, m), 1.63 (2H, m),
4.17 (2H, s), 4.19 (2H, t), 7.35 (1H, dd),
8.04 (1H, d), 8.45 (1H, d).

The compounds having the general formula (I) wherein n=0 were synthesized in similar manners as described in Example 1. The compounds obtained are shown in Examples 2-76.

EXAMPLE 2

2-[(ethoxycarbonylmethyl)thio]thiazolo[4,5-c]pyridine

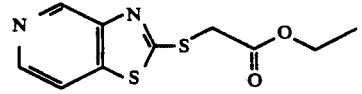

$^1$HNMR(CDCl$_3$) δ:
1.31 (3H, t), 4.21 (2H, s), 4.27 (2H, ABq),
7.73 (1H, d), 8.45 (1H, dd), 9.13 (1H, s).

EXAMPLE 3

2-[(2-di-isopropylaminoethyl)thio]thiazolo[4,5-c]pyridine

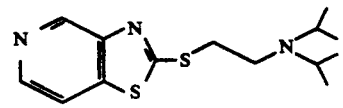

$^1$HNMR(CDCl$_3$) δ:
1.06 (12H, d), 2.88 (2H, t), 3.07 (2H, m),
3.42 (2H, t), 7.70 (1H, dd), 8.42 (1H, d),
9.09 (1H, d).

EXAMPLE 4

2-[(ethoxycarbonylmethyl)thio]-6trifluoromethyl-thiazolo[4,5-b]pyridine

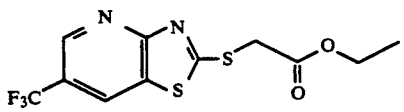

¹HNMR(CDCl₃) δ:
1.31 (3H, t), 4.25 (2H, q), 4.33 (2H, s),
8.37 (1H, s), 8.89 (1H, s).

EXAMPLE 5

2-[(2-di-isopropylamino)ethyl]thio-6trifluoromethyl-thiazolo[4,5-b]pyridine

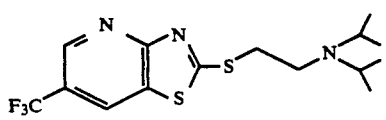

¹HNMR(CDCl₃) δ:
1.07 (12H, d), 2.91 (2H, t), 3.08 (2H, m),
3.57 (2H, t), 8.31 (1H, s), 8.83 (1H, s).

EXAMPLE 6

2-[(2-(1-methylpyrrolidin-2-yl)ethyl)thio]thiazolo[4,5-c]pyridine

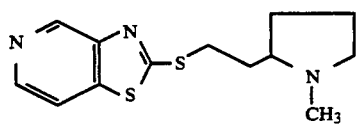

¹HNMR(CDCl₃) δ:
1.54-1.66 (1H, m), 1.68-1.88 (3H),
1.98-2.08 (1H, m), 2.11-2.30 (3H, m), 2.34 (3H, s),
3.08 (1H, dt), 3.42 (1H, dq)x2, 7.71 (1H, d),
8.44 (1H, d), 9.12 (1H, s).

EXAMPLE 7

2-[(methoxycarbonylmethyl)thio]thiazolo[5,4-d]pyrimidine

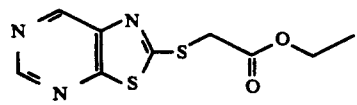

¹HNMR(CDCl₃) δ:
1.31 (3H, t), 4.20 (2H, s), 4.28 (2H, q),
9.01 (1H, s), 9.10 (1H, s).

EXAMPLE 8

2-[(2-oxopropyl)thio]thiazolo[5,4-b]pyridine

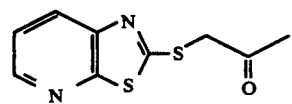

¹HNMR(CDCl₃) δ:
2.42 (3H, s), 4.25 (2H, s), 7.35 (1H, q),
8.03 (1H, d), 8.45 (1H, d).

EXAMPLE 9

2-[(crotyloxycarbonylmethyl)thio]thiazolo[5,4-b]pyridine

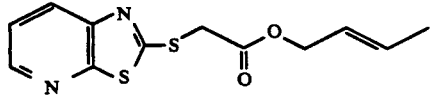

¹HNMR(CDCl₃) δ:
1.70 (3H, d), 4.20 (2H, s), 4.61 (2H, d),
5.59 (1H, m), 5.81 (1H, m), 7.35 (1H, q),
8.03 (1H, d), 8.44 (1H, d).

EXAMPLE 10

2-(geranyloxycarbonylmethyl)thio]thiazolo[5,4-b]pyridine

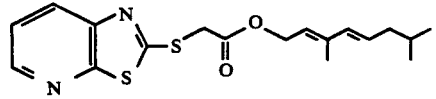

¹HNMR(CDCl₃) δ:
1.7 (6H), 2.05 (4H, m), 4.19 (2H, s), 4.70 (2H, d),
5.04 (1H, m), 5.35 (1H, m), 7.33 (1H, q),
8.03 (1H, d), 8.44 (1H, d).

EXAMPLE 11

2-[2-(2,2,6,6-tetramethylpiperidin-1-yl)ethylthio-6trifluoromethylthiazolo[4,5-b]pyridine

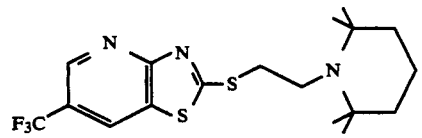

¹HNMR(CDCl₃) δ:
1.11 (12H, s), 1.44 (4H, m), 1.55 (2H, m),
2.91 (2H, m), 3.40 (2H, m), 8.32 (1H, s),
8.85 (1H, s).

EXAMPLE 12

2-[(di-isopropylaminocarbonylmethyl)thio]-thiazolo[5,4-b]pyridine

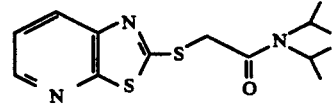

¹HNMR(CDCl₃) δ:
1.30 (6H, d), 1.42 (6H, d), 3.52-3.56 (1H, m),
4.07-4.15 (1H, m), 4.44 (2H, t), 7.36 (H, dd),
8.05 (1H, d), 8.45 (1H, d).

EXAMPLE 13

2-[2-(2,2,6,6-tetramethylpiperidin-1yl)ethyl)thio]-thiazolo[5,4-b]pyridine

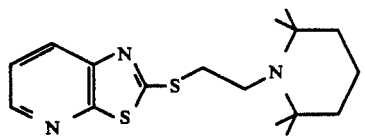

¹HNMR(CDCl₃) δ:
1.10 (12H, s), 1.42-1.55 (4H, m), 1.55 (1H, m),
1.67 (1H, m), 2.88 (2H, m), 3.27 (2H, m),
7.33 (1H, dd), 8.01 (1H, d), 8.43 (1H, d).

EXAMPLE 14

2-[(2-ethoxycarbonylethyl)thio]thiazolo[5,4-b]pyridine

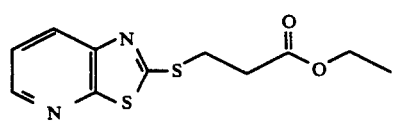

¹HNMR(CDCl₃) δ:
1.28 (3H, t), 2.92 (2H, t), 3.63 (2H, t),
4.20 (2H, q), 7.38 (1H, dd), 8.08 (1H, d),
8.45 (1H, d).

EXAMPLE 15

2-carboxymethylthiothiazolo[5,4-b]pyridine

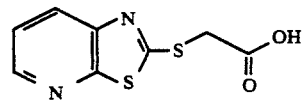

¹HNMR(CDCl₃) δ:
4.28 (2H, s), 7.54 (1H, dd), 8.22 (1H, d),
8.50 (1H, d).
EI (m/z): 221 (M⁻¹)

EXAMPLE 16

2-[(1-ethoxycarbonyl-1-methyl)ethylthio]thiazolo[5,4-b]pyridine

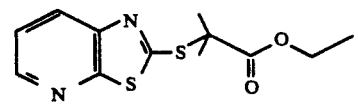

¹HNMR(CDCl₃) δ:
1.21 (3H, t), 1.78 (6H, s), 4.21 (2H, ABq),
7.36 (1H, dd), 8.08 (1H, dd), 8.48 (1H, dd).

EXAMPLE 17

2-[(allyloxycarbonylmethyl)thio]thiazolo[5,4-b]pyridine

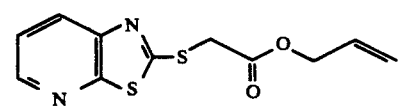

¹HNMR(CDCl₃) δ:
4.22 (2H, s), 4.69 (2H, d), 5.26 (1H, d),
5.37 (1H, d), 5.92 (1H, m), 7.36 (1H, dd),
8.05 (1H, d), 8.46 (1H, d).

EXAMPLE 18

2-[(isopropoxycarbonylmethyl)thio]thiazolo[5,4-b]pyridine

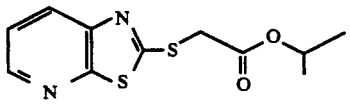

¹HNMR(CDCl₃) δ:
1.27 (6H, d), 4.13 (2H, s), 5.10 (1H, m),
7.35 (1H, dd), 8.03 (1H, d), 8.45 (1H, d).
EI (m/z): 268 (M⁺)

EXAMPLE 19

2-[(t-butoxycarbonylmethyl)thio]thiazolo[5,4-b]pyridine

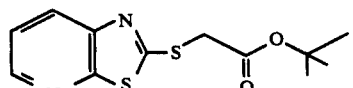

¹HNMR(CDCl₃) δ:
1.47 (9H, s), 4.08 (2H, s), 7.35 (1H, dd),
8.03 (1H, d), 8.45 (1H, d).
EI (m/z): 282 (M⁺)

EXAMPLE 20

2-[(3-ethoxycarbonyl-2-oxopropyl)thio]thiazolo[5,4-b]pyridine

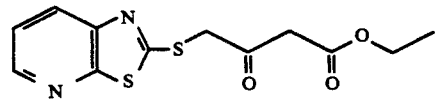

¹HNMR(CDCl₃) δ:
1.29 (3H, t), 3.76 (2H, s), 4.23 (2H, ABq),
4.33 (2H, s), 7.36 (1H, dd), 8.03 (1H, dd),
8.46 (1H, brd).

EXAMPLE 21

2-[(methoxycarbonylmethyl)thio]thiazolo[5,4-b]pyridine

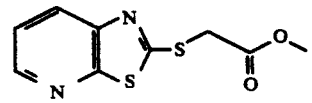

¹HNMR(CDCl₃) δ:
3.80 (3H, s), 4.20 (2H, s), 7.36 (1H, dd),
8.06 (1H, d), 8.45 (1H, d)
EI (m/z): 240 (M⁺)

EXAMPLE 22

2-[2-(2,2,6,6-tetramethylpiperidin-1-yl)ethylthio]-1Himidazo[4,5-b]pyridine

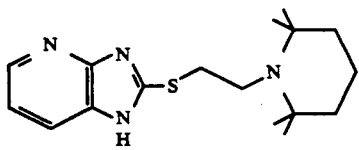

¹HNMR(CDCl₃) δ:
1.16 (12H, s), 1.65 (6H, s), 3.05 (2H, t),
3.32 (2H, t), 7.15 (1H, dd), 7.87 (1H, d),
8.30 (1H, d).
EI (m/z) 319 (M+)

EXAMPLE 23

2-[(ethoxycarbonylmethyl)thio]thiazolo[5,4-c]pyridine

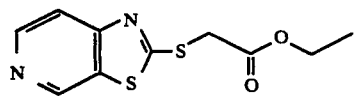

¹HNMR(CDCl₃) δ:
1.30 (3H, t), 4.21 (2H, s), 4.36 (2H, q),
7.72 (1H, d), 8.57 (1H, d), 9.04 (1H, s).

EXAMPLE 24

2-[(2-ethoxycarbonyl-2-oxoethyl)thio]thiazolo[5,4-b]pyridine

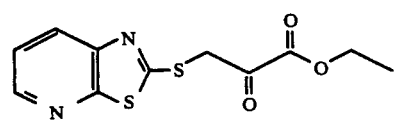

¹HNMR(DMSO-d₆) δ:
1.09 (3H, t), 4.05 (2H, m), 4.19 (2H, q),
7.52 (1H, dd), 8.19 (1H, d), 8.50 (1H, d).

EXAMPLE 25

2-[(carbamoylmethyl)thio]thiazolo[5,4-b]pyridine

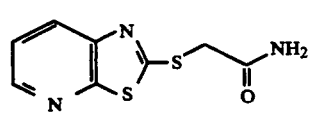

¹HNMR(DMSO-d₆) δ:
4.18 (2H, s), 7.37 (1H, brs), 7.53 (1H, dd),
7.79 (1H, brs), 8.20 (1H, dd), 8.50 (1H, dd).

EXAMPLE 26

2-[(ethoxycarbonylmethyl)thio]thiazolo[4,5-d]pyridazine

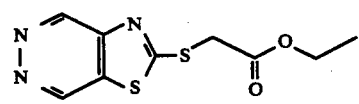

¹HNMR(CDCl₃) δ:
1.32 (3H, t), 4.25 (2H, s), 4.28 (2H, ABq),
9.60 (1H, s), 9.63 (1H, s).

EXAMPLE 27

2-[(n-propoxycarbonylmethyl)thio]thiazolo[5,4-b]pyridine

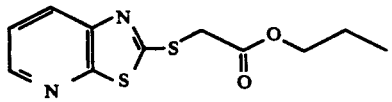

¹HNMR(CDCl₃) δ:
0.94 (3H, t), 1.68 (2H, m₆), 4.15 (2H, t),
4.18 (2H, s), 7.36 (1H, dd), 8.04 (1H, d),
8.45 (1H, d).
EI (m/z): 268 (M+)

EXAMPLE 28

4-chloro-2-[ethoxycarbonylmethyl)thio]thiazolo[4,5-d]pyridazine

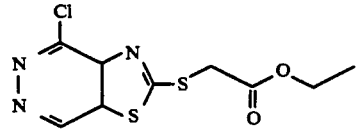

¹HNMR(CDCl₃) δ:
1.33 (3H, t), 4.27 (2H, s), 4.30 (2H, ABq),
9.52 (1H, s).

EXAMPLE 29

2-[(4-(1-cyclohexyltetrazol-5-yl)butyl)thio]thiazolo[5,4-b]pyridine

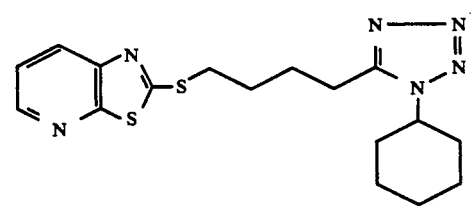

¹HNMR(CDCl₃) δ:
1.25-2.10 (14H, m), 2.90 (2H, t), 3.45 (2H, t),
4.10 (1H, m), 7.36 (1H, dd), 8.04 (1H, dd),
8.45 (1H, dd).

EXAMPLE 30

2-[(4-(1-methyltetrazol-5-yl)butyl)thio]thiazolo[5,4-b]pyridine

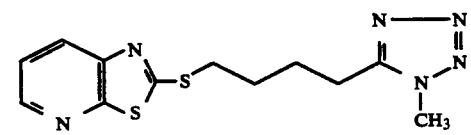

¹HNMR(CDCl₃) δ:
1.95-2.10 (4H, m), 2.92 (2H, m), 3.44 (2H, t),
4.00 (3H, s), 7.36 (1H, dd), 8.05 (1H, dd),
8.45 (1H, dd).

EXAMPLE 31

2-[(isobutoxycarbonylmethyl)thio]thiazolo[5,4-b]pyridine

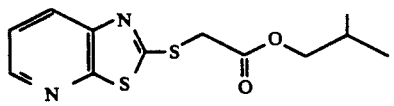

¹HNMR(CDCl₃) δ:
0.92 (6H, d), 1.96 (1H, m₇), 3.97 (2H, d),
4.19 (2H, s), 7.35 (1H, dd), 8.04 (1H, d),
8.45 (1H, d).

EI (m/z): 282 (M+)

EXAMPLE 32

2-[(n-butylcarbonylmethyl)thio]thiazolo[5,4-b]pyridine

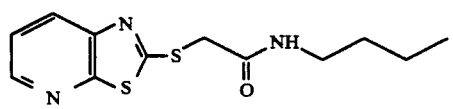

¹HNMR(CDCl₃) δ:
0.82 (3H, t), 1.26 (2H, m₆), 1.44 (2H, m₅),
3.27 (2H, m₄), 3.99 (2H, s), 7.08 (1H, s),
7.40 (1H, dd), 8.06 (1H, d), 8.49 (1H, d).
EI (m/z): 281 (M+)

EXAMPLE 33

2-methylthiothiazolo[5,4-b]pyridine

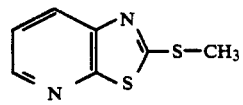

¹HNMR(CDCl₃) δ:
2.80 (3H, s), 7.35 (1H, dd), 8.06 (1H, d),
8.44 (1H, d).
EI (m/z): 182 (M+)

EXAMPLE 34

2-[(ethoxycarbonylmethyl)thio]thiazolo[4,5-b]pyridine

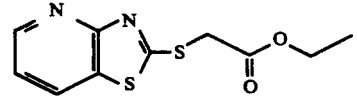

¹HNMR(CDCl₃) δ:
1.30 (3H, t), 4.25 (2H, q), 4.33 (2H, s),
7.25 (1H, dd), 8.12 (1H, dd), 8.62 (1H, dd).

EXAMPLE 35

2-[(2-di-isopropylaminomethyl)thio]thiazolo[4,5-b]pyridine

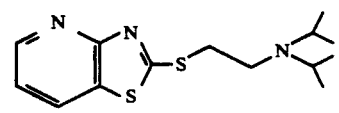

¹HNMR(CDCl₃) δ:
1.04 (12H, brs), 2.90 (2H, brs), 3.03 (2H, brs),
3.52 (2H, brs), 7.20 (1H, dd), 8.07 (1H, d),
8.60 (1H, dd).

EXAMPLE 36

2-[(ethoxycarbonylmethyl)thio]thiazolo[4,5-b]pyrazine

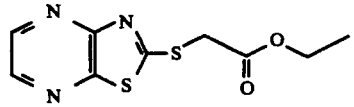

¹HNMR(CDCl₃) δ:
1.30 (3H, t), 4.25 (2H, q), 4.31 (2H, s),
8.39 (1H, d), 8.56 (1H, brs).

EXAMPLE 37

2-[(3-ethoxycarbonyl-2-propenyl)thio]thiazolo[5,4-b]pyridine

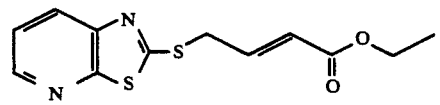

¹HNMR(CDCl₃) δ:
1.28 (3H, t), 4.14 (2H, dd), 4.19 (2H, q),
6.12 (1H, dt), 7.06 (1H, dt), 7.37 (1H, dd),
8.07 (1H, dd), 8.46 (1H, dd).

EXAMPLE 38

2-[(ethoxycarbonyl)difluoromethyl)thio]thiazolo5,4-b]pyridine

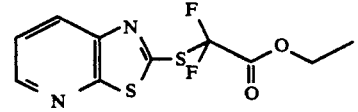

¹HNMR(CDCl₃) δ:
1.31 (3H, t), 4.37 (2H, q), 7.47 (1H, dd),
8.29 (1H, dd), 8.63 (1H, dd).

EXAMPLE 39

2-[(2-hydroxyethyl)thio]thiazolo[5,4-b]pyridine

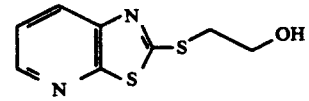

¹HNMR(CDCl₃) δ:
3.56 (2H, t), 4.06 (2H, brt), 7.36 (1H, dd),
8.04 (1H, dd), 8.46 (1H, dd).

EXAMPLE 40

2-[(2-acetoxyethyl)thio]thiazolo[5,4-b]pyridine

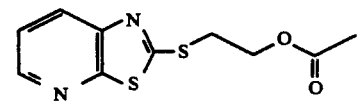

¹HNMR(CDCl₃) δ:
2.08 (3H, s), 3.64 (2H, t), 4.46 (2H, t),
7.36 (1H, dd), 8.06 (1H, dd), 8.45 (1H, dd).

EXAMPLE 41

2-[(2-(1,3-dioxo-isoindol-2-yl)ethyl)thio]thiazolo[5,4-b]pyridine

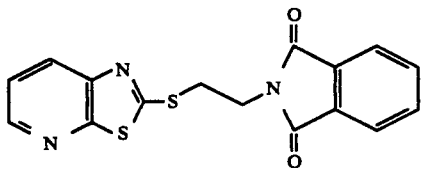

¹HNMR(CDCl₃) δ:
3.72 (2H, t), 4.21 (2H, t), 7.30 (1H, dd),
7.69 (2H, dd), 7.83 (2H, dd), 7.94 (1H, dd),
8.41 (1H, dd).

EXAMPLE 42

2-[(isopentoxycarbonylmethyl)thio]thiazolo[5,4-b]pyridine

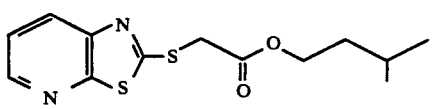

¹HNMR(CDCl₃) δ:
0.89 (6H, d), 1.54 (2H, q), 1.64 (1H, m),
4.18 (2H, s), 4.22 (2H, t), 7.36 (1H, dd),
8.04 (1H, d), 8.45 (1H, d).
EI (m/z): 296 (M)+

EXAMPLE 43

2-[(n-octyl)thio]thiazolo[5,4-b]pyridine

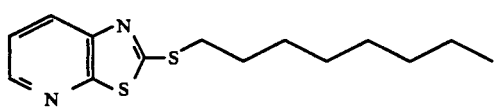

¹HNMR(CDCl₃) δ:
0.88 (3H, t), 1.27–1.36 (8H, m), 1.48 (2H, m5),
1.83 (2H, m⁵), 3.36 (2H, t), 7.34 (1H, dd),
8.04 (1H, d), 8.43 (1H, d).
EI (m/z): 280 (M)+

EXAMPLE 44

2-(isopenthylthio)thiazolo[5,4-b]pyridine

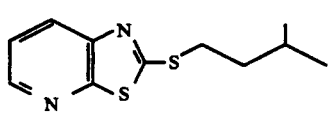

¹HNMR(CDCl₃) δ:
0.98 (6H, d), 1.69-1.82 (3H, m⁹), 3.37 (2H, t),
7.34 (1H, dd), 8.05 (1H, d), 8.43 (1H, d).
EI (m/z): 238 (M)+

EXAMPLE 45

2-[(n-octoxycarbonylmethyl)thio]thiazolo[5,4-b]pyridine

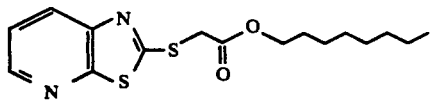

¹HNMR(CDCl₃) δ:
0.87 (3H, t), 1.22–1.28 (10H, m), 1.63 (2H, t),
4.17 (2H, s), 4.17 (2H, t), 7.36 (1H, dd),
8.04 (1H, d), 8.45 (1H, d).
EI (m/z): 338 (M)+

EXAMPLE 46

2-[(cyclopentoxycarbonylmethyl)thio]thiazolo[5,4-b]pyridine

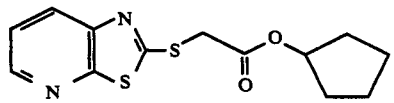

¹HNMR(CDCl₃) δ:
1.60 (2H, m), 1.71 (4H, m), 1.75 (2H, m),
4.10 (2H, s), 5.25 (1H, m), 7.36 (1H, dd),
8.03 (1H, d), 8.45 (1H, d).
EI (m/z): 294 (M)+

EXAMPLE 47

2-[(2-(2,2,6,6-tetramethylpiperidin-1-yl)ethyl)thio]oxazolo[4,5-b]pyridine

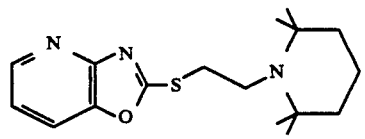

¹HNMR(CDCl°) δ:
1.11 (12H, s), 1.43 (4H, t), 1.51–1.54 (2H, m),
2.92 (2H, m⁷), 3.27 (2H, m⁷), 7.17 (1H, dd),
7.68 (1H, d), 8.46 (1H, d).
EI (m/z): 319 (M⁻¹)+

EXAMPLE 48

2-[(2-(2,2,6,6-tetramethylpiperidin-1-yl)ethyl)thio]oxazolo[5,4-b]pyridine

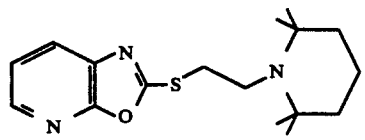

¹HNMR(CDCl₃) δ:
1.10 (12H, s), 1.43 (4H, t), 1.53–1.57 (2H, m),
2.88 (2H, m;), 3.23 (2H, m;), 7.25 (1H, dd),
7.85 (1H, d), 8.20 (1H, d).
EI (m/z): 320 (M)+

EXAMPLE 49

2-[(methoxycarbonylmethyl)thio]oxazolo[4,5-b]pyridine

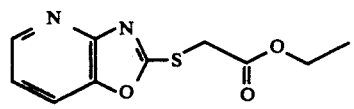

¹HNMR(CDCl₃) δ:
1.31 (3H, t), 4.20 (2H, s), 4.26 (2H, q),
7.20 (1H, dd), 7.73 (1H, d), 8.47 (1H, d).
EI (m/z): 238 (M)+

EXAMPLE 50

2-[(ethoxycarbonylmethyl)thio]oxazolo[5,4-b]pyridine

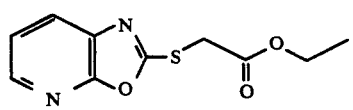

¹HNMR(CDCl₃) δ:
1.30 (3H, t), 4.12 (2H, s), 4.27 (2H, q),
7.28 (1H, dd), 7.88 (1H,..d), 8.23 (1H, d).
EI (m/z): 238 (M)+

EXAMPLE 51

2-[(2-di-isopropylaminoethyl)thio]oxazolo[4,5-b]pyridine

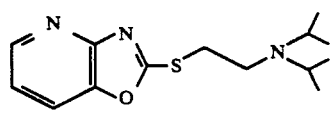

¹HNMR(CDCl₃) δ:
1.07 (12H, d), 2.90 (2H, t), 3.07 (2H, m),
3.43 (2H, t), 7.16 (1H, dd), 7.67 (1H, d),
8.45 (1H, d).
EI (m/z): 280 (M)+

EXAMPLE 52

2-[(2-di-isopropylaminoethyl)thio]oxazolo[5,4-b]pyridine

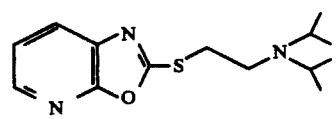

¹HNMR(CDCl₃) δ:
1.05 (12H, d), 2.88 (2H, t), 3.06 (2H, m⁷),
3.37 (2H, t), 7.26 (1H, dd), 7.84 (1H, d),
8.19 (1H, d).
EI (m/z): 280 (M)+

EXAMPLE 53

2-[(N-cyclohexylcarbamoylmethyl)thio]thiazolo[5,4-b]pyridine

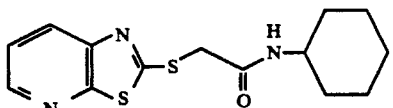

¹HNMR(CDCl₃) δ:
1.08-1.86 (10H), 3.78 (1H, m), 3.96 (2H, s),
7.40 (1H, dd), 8.06 (1H, dd), 8.49 (1H, dd).
EI (m/z): 307 (M)+

EXAMPLE 54

2-[(N-methylcarbamoylmethyl)thio]thiazolo[5,4-b]pyridine

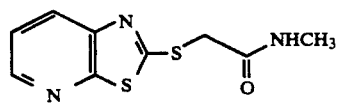

¹HNMR(CDCl₃) δ:
2.84 (3H, d), 4.02 (2H, s), 7.00 (1H, brs),
7.40 (1H, dd), 8.09 (1H, dd), 8.49 (1H, dd).
EI (m/z): 239 (M)+

EXAMPLE 55

2-[((1-cyclohexyltetrazol-5-yl)methyl)thio]thiazolo[5,4-b]pyridine

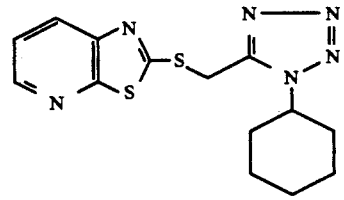

¹HNMR(CDCl₃) δ:
1.25-2.15 (10H), 4.55 (1H, m), 4.95 (2H, s),
7.41 (1H, dd), 8.07 (1H, dd), 8.50 (1H, dd).
EI (m/z): 333 (M+1)+

EXAMPLE 56

2-[((1-methyltetrazol-5-yl)methyl)thio]thiazolo[5,4-b]pyridine

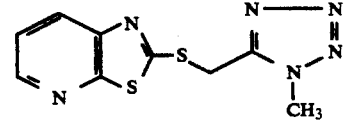

¹HNMR(CDCl₃) δ:
4.24 (3H, s), 4.91 (2H, s), 7.40 (1H, dd),
8.06 (1H, dd), 8.50 (1H, dd).
EI (m/z): 264 (M)+

EXAMPLE 57

2-[(2-ethoxyethyl)thio]thiazolo[5,4-b]pyridine

¹HNMR(CDCl₃) δ:
1.23 (3H, t), 3.56-3.62 (4H, m), 3.82 (2H, t),
7.35 (1H, dd), 8.06 (1H, d), 8.46 (1H, d).
EI (m/z): 240 (M⁺)

EXAMPLE 58

6-chloro-2-[(2-ethoxyethyl)thio]thiazolo[5,4-b]pyridine

¹HNMR(CDCl₃) δ:
1.22 (3H, t), 3.52-3.61 (4H, m), 3.80 (2H, t),
8.03 (1H, d), 8.40 (1H, d).
EI (m/z). ° , ᴛᴍ (M⁺)

EXAMPLE 59

2-[(2-ethoxyethyl)thio]thiazolo[4,5-c]pyridine

¹HNMR(CDCl₃) δ:
1.22 (3H, t), 3.58 (2H, q), 3.62 (2H, t),
3.82 (2H, t), 7.72 (1H, dd), 8.44 (1H, d),
9.11 (1H, s).
EI (m/z): 240 (M⁺)

EXAMPLE 60

2-[(2-ethoxyethyl)thio]1H-imidazo[4,5-b]pyridine

¹HNMR(CDCl₃) δ:
1.28 (3H, t), 3.53 (2H, t), 3.65 (2H, q),
3.89 (2H, t), 7.18 (1H, dd), 7.92 (1H, d),
8.30 (1H, d).
EI (m/z): 223 (M⁺)

EXAMPLE 61

2-[2(piridin-2-yl)-ethylthio]thiazolo[5,4-b]pyridine

¹HNMR(CDCl₃) δ:
3.32 (2H, t), 3.81 (2H, t), 3.81 (2H, t),
7.16 (1H, q), 7.22 (1H, d), 7.34 (1H, d),
7.62 (1H, m), 8.06 (1H, q), 8.44 (1H, q),
8.58 (1H, d).
EI (m/z): 273 (M⁺)

EXAMPLE 62

2-[(2-oxazolidin-5-yl)-methylthio]thiazolo[5,4-b]pyridine

¹HNMR(CDCl₃) δ:
3.54 (1H, dd), 3.64 (1H, dd), 3.82 (1H, t),
3.88 (1H, dd), 5.11 (1H, m), 7.38 (1H, dd),
8.06 (1H, d), 8.47 (1H, d).
EI (m/z): 267 (M⁺)

EXAMPLE 63

2-[(3-methyl-2-butenyl)thio]thiazolo[5,4-b]pyridine

¹HNMR(CDCl₃) δ:
1.78 (6H, d), 4.02 (2H, d), 5.41 (1H, m),
7.35 (1H, dd), 8.05 (1H, d), 8.44 (1H, d).
EI (m/z): 236 (M⁺)

EXAMPLE 64

2-[(ethoxycarbonylmethyl)thio]thiazolo[5,4-b]cyridine

¹HNMR(CDCl₃) δ:
1.30 (3H, t), 4.18 (2H, s), 4.26 (2H, q),
7.36 (1H, dd), 8.05 (1H, d), 8.45 (1H, d).
EI (m/z): 254 (M⁺)

EXAMPLE 65

2-[(2-morpholinoethyl)thio]thiazolo[5,4-b]pyridine

¹HNMR(CDCl₃) δ:
2.55 (4H, t), 2.81 (2H, t), 3.55 (2H, t),
3.72 (4H, t), 7.35 (1H, dd), 8.03 (1H, d),
8.44 (1H, d).
EI (m/z): 281 (M⁺)

EXAMPLE 66

2-[(2-morpholinoethyl)thio]thiazolo[4,5-c]pyridine

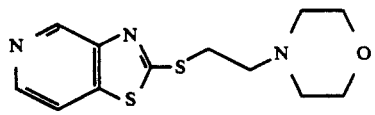

¹HNMR(CDCl₃) δ:
2.53 (4H, t), 2.82 (2H, t), 3.59 (2H, t),
3.72 (4H, t), 7.72 (1H, d), 8.43 (1H, d),
9.12 (1H, s).
EI (m/z): 281 (M+)

EXAMPLE 67

2-[(2-N,N-diethylaminoethyl)thio]thiazolo[5,4-b]pyridine

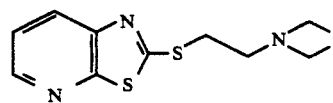

¹HNMR(CDCl₃) δ:
1.08 (4H, t), 2.63 (4H, q), 2.89 (2H, t),
3.47 (2H, t), 7.34 (1H, dd), 8.03 (1H, d),
8.43 (1H, d).
EI (m/z): 267 (M+)

EXAMPLE 68

6-chloro-2-[(2-morpholinoethyl)thio]thiazolo[5,4-b]pyridine

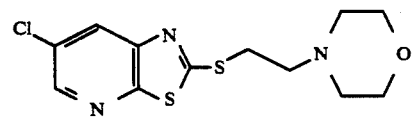

¹HNMR(CDCl₃) δ:
2.56 (4H, t), 2.82 (2H, t), 3.53 (2H, t),
3.71 (4H, t), 8.00 (1H, d), 8.39 (1H, d).
EI (m/z): 315 (M+)

EXAMPLE 69

2-[(2-morpholinoethyl)thio]imidazopyridine

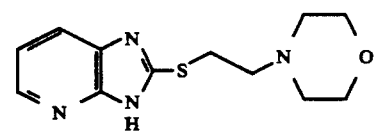

¹HNMR(CDCl₃) δ:
2.62 (4H, t), 2.90 (2H, t), 3.43 (2H, t),
3.81 (4H, t), 7.17 (1H, dd), 7.90 (1H, d),
8.30 (1H, d).
EI (m/z): 264 (M+)

EXAMPLE 70

2-[(2-(1-methylpyrrolidin-2-yl)ethyl)thio]thiazolo[5,4-b]pyridine

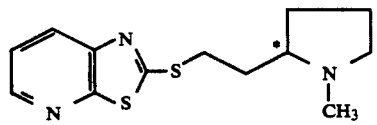

¹HNMR(CDCl₃) δ:
1.55–1.64 (1H, m), 1.67–1.87 (4H, m),
1.97–2.06 (1H, m), 2.10–2.27 (2H, m),
2.33 (3H, d), 3.07 (1H, t), 3.26–3.33 (1H, m),
3.42–3.49 (1H, m), 7.33 (1H, dd), 8.03 (1H, d),
8.42 (1H, d).
EI (m/z): 279 (M+)

EXAMPLE 71

2-[(2-ureidoethyl)thio]thiazolo[5,4-b]pyridine

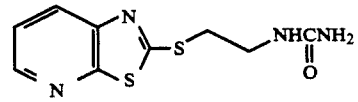

¹HNMR(CDCl₃) δ:
3.39–3.46 (4H, m), 5.54 (2H, s), 6.30 (1H, s),
7.52 (1H, dd), 8.21 (1H, d), 8.49 (1H, d).
EI (m/z): 254 (M+)

EXAMPLE 72

2-[(1-methylpiperidin-3-yl)methylthio]thiazolo5,4-b]pyridine

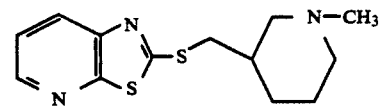

¹HNMR(CDCl₃) δ:
1.09 (1H, m), 1.56–1.66 (1H, m), 1.68–1.77 (1H, m),
1.83 (1H, t), 1.89–1.98 (2H, m), 2.06–2.16 (1H, m),
2.27 (3H, d), 2.75 (1H, d), 2.96 (1H, d),
3.33 (2H, dd), 7.34 (1H, dd), 8.04 (1H, d),
8.43 (1H, d).
EI (m/z): 279 (M+)

EXAMPLE 73

2-[(1-methylpiperidin-4-yl)thio]5,4-b]pyridine

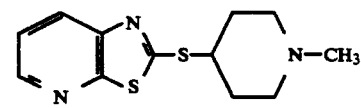

¹HNMR(CDCl₃) δ:
1.89 (2H, m), 2.23–2.27 (4H, m), 2.30 (3H, s),
2.77–2.80 (2H, m), 3.98–4.01 (1H, m), 7.35 (1H, dd),
8.06 (1H, d), 8.44 (1H, d).
EI (m/z): 265 (M+)

EXAMPLE 74

2-[(2-di-isopropylaminoethyl)thio]thiazolo[5,4-b]pyridine

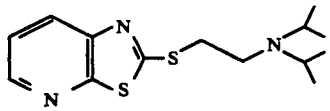

¹HNMR(CDCl₃) δ:
1.04 (6H, d), 1.06 (6H,
3.06 (2H, m), 3.38 (2H, t), 7.34 (1H, dd),
8.02 (1H, d), 8.43 (1H, d).
EI (m/z): 295 (M+)

EXAMPLE 75

2-[(3-(1-methylpiperazin-4-yl)propyl)thio]thiazolo[5,4-b]pyridine

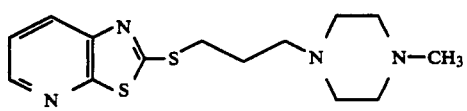

¹HNMR(CDCl₃) δ:
2.02 (2H, q), 2.29 (3H, s), 2.50–2.53 (8H, m),
2.51 (2H, t), 3.41 (2H, t), 7.35 (1H, dd),
8.03 (1H, d), 8.44 (1H, d).
EI (m/z): 308 (M+)

EXAMPLE 76

2-[(2-di-n-butylaminoethyl)thio]thiazolo[5,4-b]pyridine

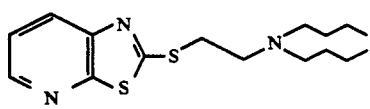

¹HNMR(CDCl₃) δ:
0.93 (6H, t), 1.30–1.39 (4H, m), 1.47 (4H, m),
2.53 (4H, m), 2.90 (2H, m), 3.50 (2H, m),
7.34 (1H, dd), 8.02 (1H, d), 8.43 (1H, d).
EI (m/z): 323 (M+)

EXAMPLE 77

2-[(ethoxycarbonylmethyl)thio)methyl]thiazolo[5,4-b]pyridine

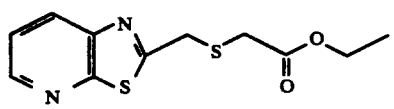

2-chloromethyl-thiazolo[5,4-b]pyridine (1.37 g, 7.43 mmol) and triethylamine (827 mg, 8.17 mmol) were dissolved in methylene chloride (10 ml), and ethyl thioglycolate (981 mg, 8.17 mmol) was added dropwise to the solution, while applying ice-cooling and agitation. After the dropwise addition had been completed, the reaction solution was cooled down to room temperature and then stirred for 5 hours. The reaction solution was diluted with chloroform (200 ml), washed with a saturated brine solution (100 ml), dried over anhydrous magnesium sulfate and distilled under reduced pressure to remove the solvent. The residue was purified by silica gel column chromatography with hexane-ethyl acetate (2:1) to obtain the title compound as a colorless oily material, yield: 1.7 g (85%).

¹HNMR(CDCl₃) δ:
1.27 (3H, t), 3.35 (2H, s), 4.18 (2H, q),
4.26 (2H, s), 7.43 (1H, dd), 8.22 (1H, dd),
8.57 (1H, d).

EXAMPLE 78

2-[(2-di-isopropylaminoethyl)thiomethyl]thiazolo[5,4-b]pyridine

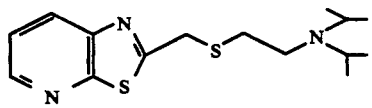

The title compound was synthesized in similar manners as described in Example 77.

¹HNMR(CDCl₃) δ:
0.96 (12H, d), 2.40–2.70 (4H, m), 2.95 (2H, m),
4.14 (2H, s), 7.41 (1H, dd), 8.17 (1H, dd),
8.56 (1H, dd).

EXAMPLE 79

2-[(n-butoxycarbonylmethyl)sulfinyl]thiazolo[5,4-b]pyridine

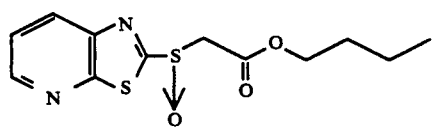

Dissolved in 50 ml of methylene chloride was 18.5 g of the compound obtained in Example 1, and the solution was cooled down to −10° C. 16.2 g of m-chloroperbenzoic acid (with a 70% purity) was added to the solution, which was in turn stirred at that temperature for 40 minutes. Ethyl acetate (600 ml) was added to the solution, which was then washed once with an aqueous solution of sodium thiosulfate, three times with sodium hydrogencarbonate and once with water, dried over magnesium sulfate, and distilled to remove the solvent. The residue was purified by silica gel column chromatography, and eluting with n-hexane-ethyl acetate (5:3 to 3:1) to obtain the title compound (13.4 g).

¹HNMR(CDCl₃) δ:
0.88 (3H, t), 1.32 (2H, m), 1.60 (2H, m),
4.14 (1H, d), 4.21 (2H, t), 4.26 (1H, d),
7.55 (1H, dd), 8.32 (1H, d), 8.70 (1H, d).

The compounds having the general formula (I) wherein n=1 were synthesized in similar manners as described in Example 79. The compounds obtained are shown in Examples 80–128.

EXAMPLE 80

2-[(ethoxycarbonylmethyl)sulfinyl]thiazolo[4,5-c]pyridine

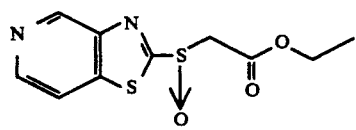

¹HNMR(CDCl₃) δ:
1.27 (3H, t), 4.15 (1H, d), 4.27 (1H, d),
4.27 (2H, ABq), 7.99 (1H, d), 8.66 (1H, d),
9.40 (1H, s).

EXAMPLE 81

2-[(ethoxycarbonylmethyl)sulfinyl]-6-trifluoromethyl-thiazolo[4,5-b]pyridine

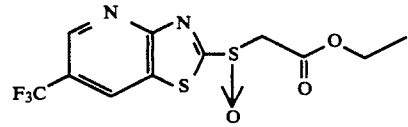

¹HNMR(CDCl₃) δ:
1.29 (3H, t), 4.18 (1H, d), 4.28 (2H, q),
4.37 (1H, d), 8.71 (1H, s), 9.09 (1H, s).

EXAMPLE 82

2-[(ethoxycarbonylmethyl)sulfinyl]thiazolo5,4-d]pyrimidine

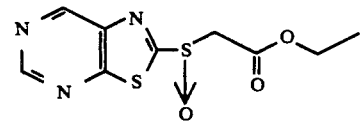

¹HNMR(CDCl₃) δ:
1.28 (3H, t), 4.17 (1H, d), 4.27 (2H, q),
4.28 (1H, d), 9.23 (1H, s), 9.41 (1H, s).

EXAMPLE 83

2-[(2-oxopropyl)sulfinyl]thiazolo[5,4-b]pyridine

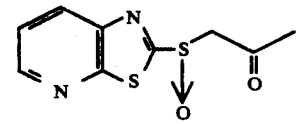

¹HNMR(CDCl₃) δ:
2.39 (3H, s), 4.22 (1H, d), 4.36 (1H, d),
7.55 (1H, dd), 8.31 (1H, d), 8.70 (1H, d).

EXAMPLE 84

2-[(crotyloxycarbonylmethyl)sulfinyl]thiazolo[5,4-b]pyridine

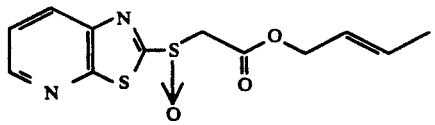

¹HNMR(CDCl₃) δ:
1.69 (3H, d), 4.13 (1H, d), 4.25 (1H, d),
7.53 (1H, dd), 8.32 (1H, d), 8.71 (1H, d).

EXAMPLE 85

2-[((6,7-epoxy)qeranyloxycarbonylmethyl)sulfinyl]-thiazolo[5,4-b]pyridine

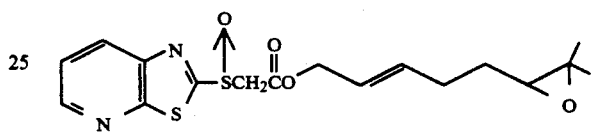

¹HNMR(CDCl₃) δ:
1.23 (3H, s), 1.30 (3H, s), 1.62 (3H, s),
1.63 (2H, m), 2.12 (2H, m), 2.69 (1H, t), 4.12 (1H, d),
4.26 (1H, d), 4.73 (2H, d), 5.34 (1H, m), 7.54 (1H, dd),
8.30 (1H, d), 8.70 (1H, d).

EXAMPLE 86

2-[(di-isopropylaminocarbonylmethyl)sulfinyl]-thiazolo[5,4-b]pyridine

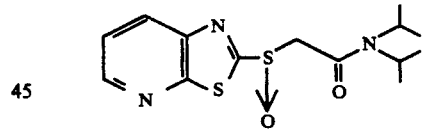

¹HNMR(CDCl₃) δ:
1.24 (6H, d), 1.43 (6H, t), 3.52-3.59 (1H, m),
3.81-3.87 (1H, m), 4.24 (2H, t), 4.36 (1H, d),

EXAMPLE 87

2-[(2-ethoxycarbonylethyl)sulfinyl]thiazolo[5,4-b]pyridine

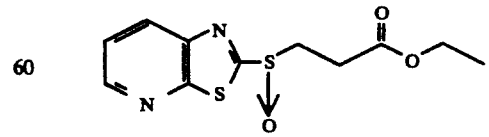

¹HNMR(CDCl₃) δ:
1.24 (3H, t), 2.63-2.71 (1H, m), 2.96-3.04 (1H, m),
3.42-3.49 (1H, m), 3.64-3.71 (1H, m), 4.13 (2H, q),
7.55 (1H, dd), 8.33 (1H, d), 8.70 (1H, d).

EXAMPLE 88

2-[(1-ethoxycarbonyl-1-methyl)ethylsulfinyl]-thiazolo[5,4-b]pyridine

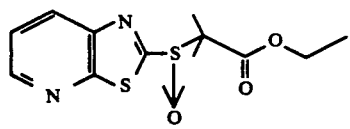

¹HNMR(CDCl₃) δ:
1.30 (3H, t), 1.48 (3H, s), 1.72 (3H, s),
4.28 (1H, ABq)×2, 7.51 (1H, dd), 8.29 (1H, dd),
8.68 (1H, dd).

EXAMPLE 89

2-[(allyloxycarbonylmethyl)sulfinyl]thiazolo[5,4-b]pyridine

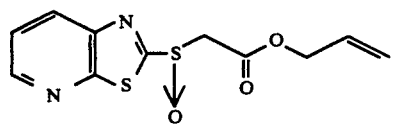

¹HNMR(CDCl₃) δ:
4.23 (2H, ABq), 4.70 (2H, d), 5.25 (1H, dd),
5.32 (1H, dd), 5.86 (1H, m), 7.55 (1H, dd),
8.33 (1H, d), 8.71 (1H, d).

EXAMPLE 90

2-[(iso-propoxycarbonylmethyl)sulfinyl]thiazolo[5,4-b]pyridine

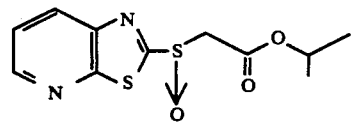

¹HNMR(CDCl₃) δ:
1.25 (6H, d), 4.12 (1H, d), 4.22 (1H, d),
5.11 (1H, m), 7.53 (1H, dd), 8.32 (1H, d),
8.70 (1H, d).
EI (m/z): 285 (M+)

EXAMPLE 91

2-[(t-butoxycarbonylmethyl)sulfinyl]thiazolo[5,4-b]pyridine

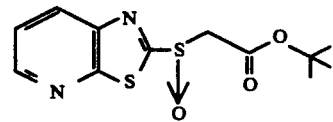

¹HNMR(CDCl₃) δ:
1.46 (9H, s), 4.06 (1H, d), 4.17 (1H, d),
7.54 (1H, dd), 8.32 (1H, d), 8.70 (1H, d).
EI (m/z): 299 (M+¹)

EXAMPLE 92

2-[(3-ethoxycarbonyl-2-oxopropyl)sulfinyl]thiazolo[5,4-b]pyridine

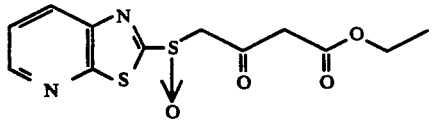

¹HNMR(CDCl₃) δ:
1.28 (3H, t), 3.66 (2H, ABq), 4.20 (2H, ABq),
4.35 (1H, d), 4.63 (1H, d), 7.55 (1H, dd),
8.33 (1H, dd), 8.71 (1H, dd).

EXAMPLE 93

2-[(methoxycarbonylmethyl)sulfinyl]thiazolo[5,4-b]pyridine

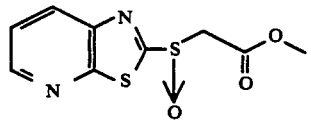

¹HNMR(CDCl₃) δ:
3.81 (3H, s), 4.15 (1H, d), 4.26 (1H, d),
7.55 (1H, dd), 8.33 (1H, d), 8.71 (1H, d).
EI (m/z): 256 (M+)

EXAMPLE 94

2-[(ethoxycarbonylmethyl)sulfinyl]thiazolo[5,4-c]pyridine

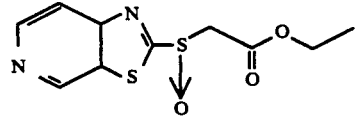

¹HNMR(CDCl₃) δ:
1.27 (3H, t), 4.15 (1H, d), 4.22-4.3 (3H, m),
7.97 (1H, d), 8.76 (1H, d), 9.38 (1H, s).

EXAMPLE 95

2-[(2-ethoxycarbonyl-2-oxoethyl)sulfinyl]thiazolo[5,4-b]pyridine

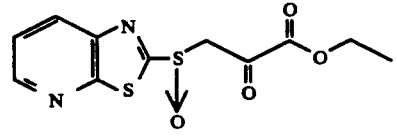

¹HNMR(CDCl₃) δ:
1.42 (3H, t), 4.40 (1H, d), 4.42 (1H, d),
4.46 (2H, ABq), 7.50 (1H, dd), 8.34 (1H, dd),
8.34 (1H, dd), 8.66 (1H, d).

EXAMPLE 96

2-[(ethoxycarbonylmethyl)sulfinyl]thiazolo[4,5-d]pyridazine

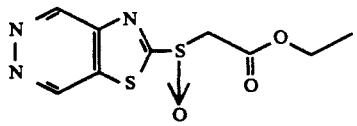

¹HNMR(CDCl₃) δ:
1.31 and 1.32 (3H, t), 4.20 and 4.22 (2H, s),
4.27 (1H, ABq)×2, 8.59 and 8.64 (1H, d), 8.81 and 8.86 (1H, brs).

EXAMPLE 97

2-[(n-propoxycarbonylmethyl)sulfinyl]thiazolo[5,4-b]pyridine

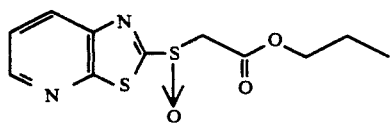

¹HNMR(CDCl₃) δ:
0.91 (3H, t), 1.65 (2H, m₅), 4.14 (1H, d),
4.17 (2H, t), 4.26 (1H, d), 7.54 (1H, dd),
8.32 (1H, d), 8.70 (1H, d).
EI (m/z): 285 (M⁺)

EXAMPLE 98

4-chloro-2-(ethoxycarbonylmethyl)sulfinyl]-thiazolo[4,5-d]pyridazine

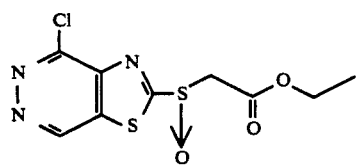

¹HNMR(CDCl₃) δ:
1.30 (3H, t), 4.19-4.37 (4H, m), 9.80 (1H, s).

EXAMPLE 99

2-[(4-(1-cyclohexyltetrazol-5-yl)butyl)sulfinyl]-thiazolo[5,4-b]pyridine

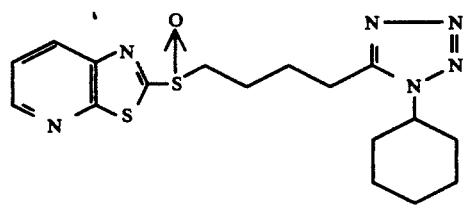

¹HNMR(CDCl₃) δ:
1.24-2.20 (14H, m), 2.87 (2H, m), 3.24-3.40 (2H, m),
4.10 (1H, m), 7.55 (1H, dd), 8.32 (1H, dd),
8.70 (1H, dd).

EXAMPLE 100

2-[(4-(1-methyltetrazol-5-yl)butyl)sulfinyl]thiazolo[5,4-b]pyridine

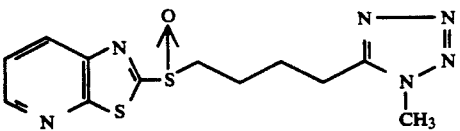

¹HNMR(CDCl₃) δ:
1.80-2.22 (4H, m), 2.89 (1H, t)x2, 3.24-3.41 (2H, m),
4.00 (3H, s), 7.55 (1H, dd),
8.32 (1H, dd), 8.70 (1H, dd).

EXAMPLE 101

2-[(isobutoxycarbonylmethyl)sulfinyl]thiazolo[5,4-b]pyridine

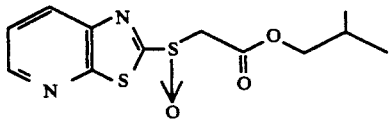

¹HNMR(CDCl₃) δ:
0.90 (6H, t), 1.93 (1H, m;), 4.00 (2H, m7),
4.16 (1H, d), 4.27 (1H, d), 7.55 (1H, dd),
8.32 (1H, d), 8.71 (1H, d).
EI (m/z): 299 (M+1)⁺

EXAMPLE 102

2-[(n-butylaminocarbonylmethyl)sulfinyl]thiazolo[5,4-b]pyridine

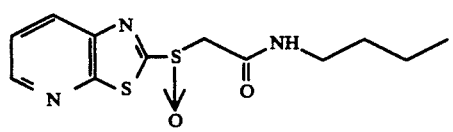

¹HNMR(CDCl₃) δ:
0.87 (3H, t), 1.26-1.32 (2H, m₁₂), 1.46 (2H, m₅),
3.25 (2H, m₅), 3.89 (1H, d), 4.12 (1H, d),
6.81 (1H, s), 7.55 (1H, dd), 8.34 (1H, d),
8.69 (1H, d).
EI (m/z): 297 (M⁺)

EXAMPLE 103

2-methylsulfinylthiazolo[5,4-b]pyridine

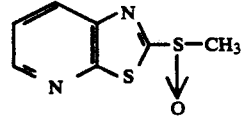

¹HNMR(CDCl₃) δ:
3.11 (3H, s), 7.54 (1H, dd), 8.32 (1H, d),
8.70 (1H, d).
EI (m/z): 198 (M⁺)

EXAMPLE 104

2-[(ethoxycarbonylmethyl)sulfinyl]thiazolo[4,5-b]pyridine

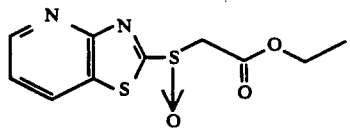

¹HNMR(CDCl₃) δ:
1.27 (3H, t), 4.16 (1H, d), 4.28 (2H, q),
4.34 (1H, d), 7.48 (1H, dd), 8.42 (1H, dd),
8.85 (1H, dd).

EXAMPLE 105

2-[(ethoxycarbonylmethyl)sulfinyl]thiazolo[4,5-b]pyrazine

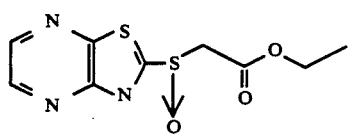

¹HNMR(CDCl₃) δ:
1.27 (3H, t), 4.19 (1H, d), 4.28 (2H, q),
4.35 (1H, d), 8.69 (1H, d), 8.81 (1H, d).

EXAMPLE 106

2-[(ethoxycarbonylmethyl)sulfinyl)methyl]thiazolo[5,4-b]pyridine

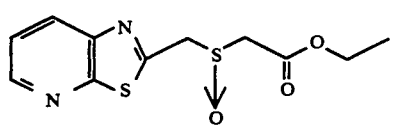

¹HNMR(CDCl₃) δ:
1.32 (3H, t), 3.77 (1H, d), 4.03 (1H, d),
4.28 (2H, q), 4.60 (1H, d), 4.77 (1H, d),
7.47 (1H, dd), 8.30 (1H, dd), 8.63 (1H, dd).

EXAMPLE 107

2-[(3-ethoxycarbonyl-2-propenyl)sulfinyl]thiazolo[5,4-b]pyridine

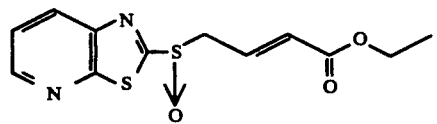

¹HNMR(CDCl₃) δ:
1.26 (3H, t), 4.01 (1H, ddd), 4.17 (2H, q, including 1H, unresolved), 6.07 (1H, dt), 6.83 (1H, quint), 7.55 (1H, dd), 8.33 (1H, dd), 8.71 (1H, dd).

EXAMPLE 108

2-[[(ethoxycarbonyl)difluoromethyl)sulfinyl]-thiazolo[5,4-b]pyridine

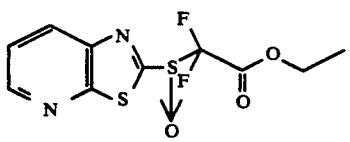

¹HNMR(CDCl₃) δ:
1.34 (3H, t), 4.40 (2H, q), 7.46 (1H, dd),
7.98 (1H, dd), 8.33 (1H, dd).

EXAMPLE 109

2-[(2-hydroxyethyl)sulfinyl]thiazolo[5,4-b]pyridine

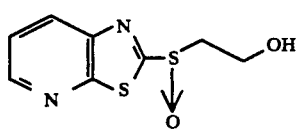

¹HNMR(CDCl₃) δ:
3.57-3.77 (2H, m), 4.89 (1H, m), 5.07 (1H, m),
7.31 (1H, ddd), 7.88 (1H, ddd), 8.37 (1H, ddd).

EXAMPLE 110

2-[(2-acetoxyethyl)sulfinyl]thiazolo[5,4-b]pyridine

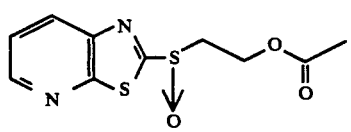

¹HNMR(CDCl₃) δ:
1.89 (3H, s), 3.50 (1H, ddd), 3.60 (1H, ddd),
4.58 (1H, ddd), 4.63 (1H, ddd), 7.54 (1H, dd),
8.32 (1H, dd), 8.70 (1H, dd).

EXAMPLE 111

2-[(2-(1,3-dioxo-isoindol-2-yl)ethyl)sulfinyl]-thiazolo[5,4-b]pyridine

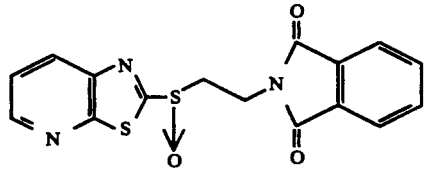

¹HNMR(CDCl₃) δ:
3.67 (2H, m), 4.29 (2H, m), 7.48 (1H, dd),
7.70 (2H, dd), 7.81 (2H, dd), 8.21 (1H, dd),
8.64 (1H, dd).

EXAMPLE 112

2-[(isopentoxycarbonylmethyl)sulfinyl]thiazolo[5,4-b]pyridine

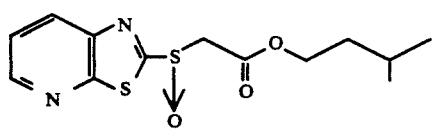

¹HNMR(CDCl₃) δ:
0.90 (6H, m), 1.50 (1H, q), 1.63 (1H, m⁷),
4.15 (1H, d), 4.25 (2H, t), 7.56 (1, dd),
8.33 (1H, d), 8.72 (1H, d).
EI (m/z): 313 (M+1)⁺

EXAMPLE 113

2-[(n-octyl)sulfinyl]thiazolo[5,4-b]pyridine

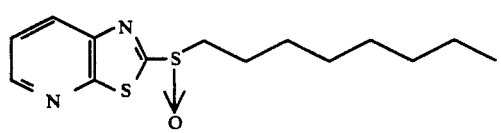

¹HNMR(CDCl₃) δ:
0.87 (3H, t), 1.22-1.36 (8H, m), 1.47 (2H, m),
1.74 (1H, m), 1.98 (1H, m), 3.23 (2H, m),
7.53 (1H, dd), 8.31 (1H, d), 8.68 (1H, d).
ET (m/z): 296 (M)⁺

EXAMPLE 114

2-(isopentylsulfinyl)thiazolo[5,4-b]pyridine

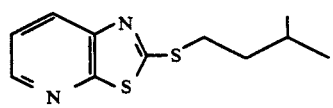

¹HNMR(CDCl₃) δ:
0.94 (6H, t), 1.58 (1H, m⁷), 1.73 (1H, m⁷)
1.88 (1H, m⁷), 3.15-3.32 (2H, m¹²), 7.53 (1H, dd),
8.32 (1H, d), 8.70 (1H, d).
EI (m/z): 355 (M+1)⁺

EXAMPLE 115

2-[(n-octoxycarbonylmethyl)sulfinyl)thiazolo[5,4-b]pyridine

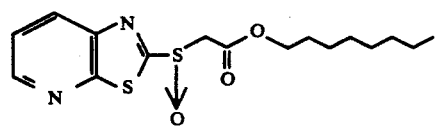

¹HNMR(CDCl₃) δ:
0.88 (3H, t), 1.27-1.54 (10H, m), 1.60 (2H, m),
4.13 (1H, d), 4.19 (2H, t), 4.25 (1H, d),
7.55 (1H, dd), 8.32 (1H, d), 8.70 (1H, d).
EI (m/z): 355 (M+1)⁺

EXAMPLE 116

2-[(cyclopentoxycarbonylmethyl)sulfinyl]thiazolo[5,4-b]pyridine

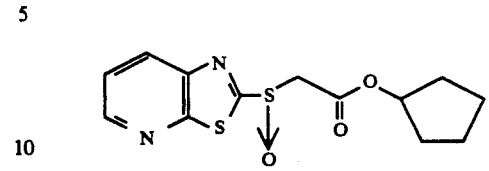

¹HNMR(CDCl₃) δ:
1.54-1.73 (6H, m), 1.80-1.90 (2H, m), 4.11 (1H, d),
4.22 (1H, d), 7.55 (1H, dd) 8.32 (1H, d),
8.70 (1H, d).
EI (m/z): 310 (M)⁺

EXAMPLE 117

2-[(N-cyclohexylcarbamoylmethyl)sulfinyl]-thiazolo[5,4-b]pyridine

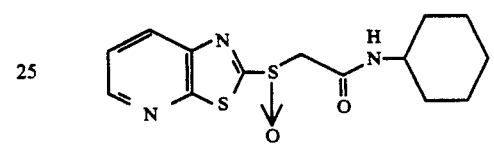

¹HNMR(CDCl₃) δ:
1.21-1.90 (10H), 3.75 (1H, m), 3.86 (1H, d),
4.12 (1H, d), 6.73 (1H, d), 7.55 (1H, dd),
8.34 (1H, dd), 8.70 (1H, dd).
EI (m/z): 323 (M)⁺

EXAMPLE 118

2-[(N-methylcarbamoylmethyl)sulfinyl]thiazolo[5,4-b]pyridine

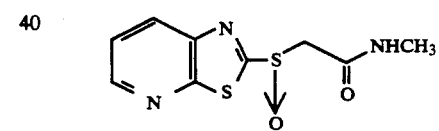

¹HNMR(CDCl₃) δ:
2.64 (3H, d), 4.10 (1H, d), 4.22 (1H, d),
7.72 (1H, dd), 8.30 (1H, brs), 8.54 (1H, d),
8.75 (1H, brd).
EI (m/z): 255 (M)⁺

EXAMPLE 119

2-[((1-cyclohexyltetrazol-5-yl)methyl)sulfinyl]-thiazolo[5,4-b]pyridine

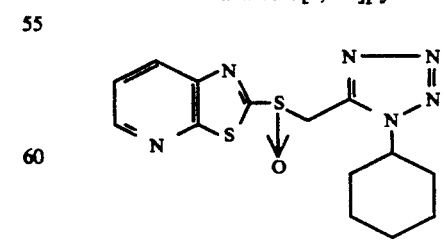

¹HNMR(CDCl₃) δ:
1.20-2.15 (10H), 4.57 (1H, m), 5.03 (1H, d),
5.50 (1H, d), 7.74 (1H, dd), 8.58 (1H, brd),
8.76 (1H, brd).
EI (m/z): 348 (M)⁺

EXAMPLE 120

2-[((1-methyltetrazol-5-yl)methyl)sulfinyl]thiazolo[5,4-b]pyridine

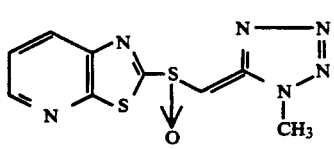

¹HNMR(CDCl₃:DMSO-d₆=5:1):
4.18 (3H, s), 4.90 (1H, d), 5.30 (1H, d),
7.63 (1H, dd), 8.42 (1H, dd), 8.71 (1H, dd).
EI (m/z): 280 (M)+

EXAMPLE 121

2-[(3-ethoxymethyl)sulfinyl]thiazolo[5,4-b]pyridine

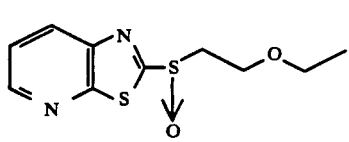

¹HNMR(CDCl₃) δ:
1.05 (3H, t), 3.37–3.44 (2H, m), 3.44–3.57 (2H, m),
3.88–4.00 (2H, m), 7.53 (1H, dd), 8.3 (1H, d),
8.69 (1H, d).
EI (m/z): 256 (M+)

EXAMPLE 122

6-chloro-2-[(2-ethoxymethyl)sulfinyl]thiazolo[5,4-b]pyridine

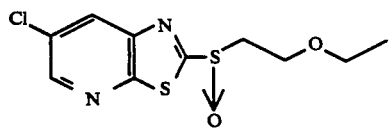

¹HNMR(CDCl₃) δ:
1.04 (3H, t), 3.36–3.44 (1H, m), 3.44–3.57 (3H, m),
8.30 (1H, s), 8.62 (1H, s).
EI (m/z): 290 (M+)

EXAMPLE 123

2-[(2-ethoxymethyl)sulfinyl]thiazolo[4,5-c]pyridine

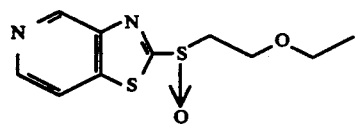

¹HNMR(CDCl₃) δ:
1.04 (3H, t), 3.37–3.44 (1H, m), 3.48 (2H, q),
3.44–3.57 (1H, m), 3.90–4.02 (2H, m), 7.96 (1H, dd),
8.63 (1H, d), 9.38 (1H, s).
EI (m/z): 256 (M+)

EXAMPLE 124

2-[(2-ethoxymethyl)sulfinyl]1H-imidazo[4,5-b]pyridine

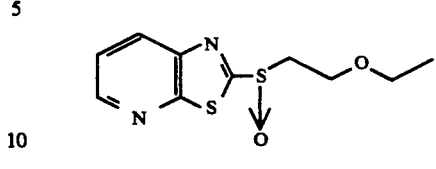

¹HNMR(CDCl₃) δ:
1.01 (3H, t), 3.46 (2H, q), 3.42–3.52 (1H, m),
3.93–4.04 (2H, m), 7.37 (1H, dd), 8.14 (1H, d),
8.75 (1H, d).
EI (m/z): 239 (M+)

EXAMPLE 125

2-[2(pyridin-2-yl)-ethylsulfinyl]thiazolo[4,5-]pyridine

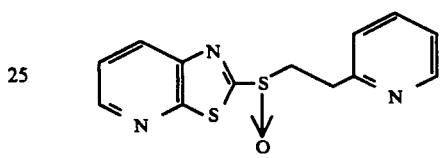

¹HNMR(CDCl₃) δ:
3.22 (1H, m), 3.45 (1H, m), 3.68 (1H, m),
3.81 (1H, m), 7.12 (1H, m), 7.20 (1H, d),
7.51 (1H, m), 7.58 (1H, m), 8.30 (1H, m),
8.48 (1H, m), 8.67 (1H, d).
EI (m/z): 289 (M)+

EXAMPLE 126

2-[(2-oxazolidion-5-yl)methylsulfinyl]thiazolo[5,4-b]pyridine

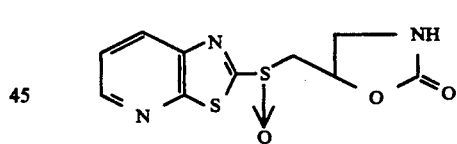

¹HNMR(CDCl₃) δ:
3.50 (1H, m), 3.63–3.91 (3H, m), 5.19–5.26 (1H, m),
7.66 (1H, m), 8.47 (1H, m), 8.70 (1H, m).
EI (m/z): 283 (M)+

EXAMPLE 127

2-[(3-methyl-2-butenyl)sulfinyl]thiazolo[5,4-b]pyridine

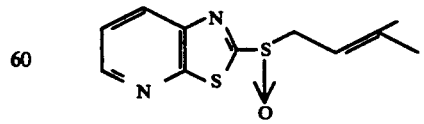

¹HNMR(CDCl₃) δ:
1.62 (3H, s), 1.78 (3H, s), 3.89 (1H, dd),
4.04 (1H, dd), 5.26 (1H, m), 7.54 (1H, dd),
8.33 (1H, d), 8.69 (1H, d).
EI (m/z): 252 (M)+

EXAMPLE 128

2-[(ethoxycarbonylmethyl)sulfinyl]thiazolo[5,4-b]pyridine

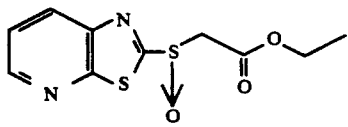

¹HNMR(CDCl₃) δ:
1.26 (3H, t), 4.14 (1H, d), 4.24 (1H, d),
4.27 (2H, q), 7.55 (1H, dd), 8.32 (1H, d),
8.71 (1H, d).
EI (m/z): 270 (M)⁺

EXAMPLE 129

2-[{2-(2,2,6,6-tetramethylpiperidin-1-yl)ethyl}sulfinyl]thiazolo[5,4-b]pyridine

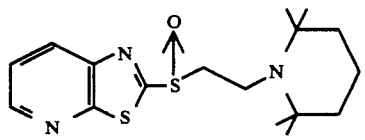

Dissolved in 7 ml of acetic acid was 3.6 g of the compound obtained in Example 13, and 1.07 ml of a 35% hydrogen peroxide solution and 50 mg of sodium tungstenate were added to the solution. The solution was stirred for 8 hours while cooled with ice or water, and was then adjusted to pH 7 by the addition of an aqueous solution of sodium hydrogencarbonate and sodium hydrogencarbonate, and extracted with 300 ml of ethyl acetate. The resulting ethyl acetate phase was washed once with an aqueous solution of sodium thiosulfate and once with a brine solution, dried over magnesium sulfate, and distilled to remove the solvent. The residue was purified by silica gel column chromatography, and eluting with n-hexane-ethyl acetate (1:1 to 1:2) to obtain the title compound (2 g).

¹HNMR(CDCl₃) δ:
1.02 (12H), 1.36–1.40 (4H, m), 1.48–1.53 (1H, m),
1.62 (1H, m), 2.81–2.89 (1H, m), 3.16–3.26 (1H, m),
3.28–3.34 (2H, m), 7.52 (1H, dd), 8.30 (1H, d),
8.68 (1H, d).

The compounds having the general formula (I) wherein n=1 were synthesized in the same manner as in Example 129. The compound having the general formula (I) wherein n=2 were synthesized in similar manners as in Example 129 except that 1.5 to 2.0 equivalents of a 35% hydrogen peroxide solution was used. The compounds obtained are shown in Examples 130–152.

EXAMPLE 130

2-[(2-di-isopropylaminomethyl)sulfinyl]thiazolo[4,5-c]pyridine

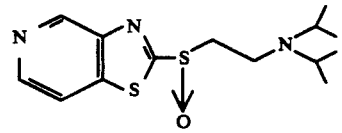

¹HNMR(CDCl₃) δ:
1.03 (6H, d), 1.10 (6H, d), 2.92–3.00 (1H, m),
3.11 (2H, m), 3.14–3.23 (2H, m), 3.36–3.44 (1H, m),
7.96 (1H, d), 8.62 (1H, d), 9.36 (1H, s).

EXAMPLE 131

2-[(2-di-isopropylamino)methyl]sulfinyl-6trifluoromethylthiazolo[4,5-b]pyridine

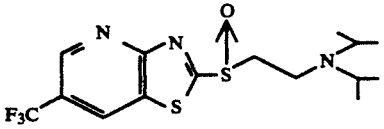

¹HNMR(CDCl₃) δ:
1.03 (3H, s), 1.04 (3H, s), 1.10 (3H, s),
1.11 (3H, s), 3.01 (1H, m), 3.05–3.25 (4H, m),
3.50 (1H, m), 8.68 (1H, s), 9.05 (1H, s).

EXAMPLE 132

2-[2-(1-methylpyrrolidin-2-yl)ethylsulfinyl]thiazolo4,5-c]pyridine

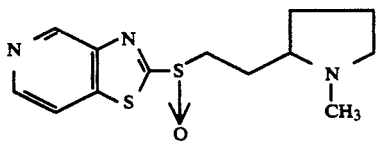

¹HNMR(CDCl₃) δ:
1.5–1.8 (5H), 1.96–2.24 (3H), 2.27 and 2.30 (3H, s),
2.98–3.43 (3H, m), 7.96 (1H, dd), 8.63 (1H, d),
9.38 (1H, s).

EXAMPLE 133

2-(2,2,6,6-tetramethylpiperidin-1-yl)methyl]sulfinyl]-6-trifluoromethylthiazolo[4,5-b]pyridine

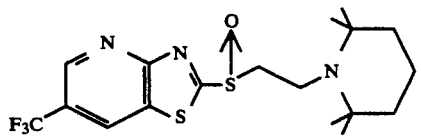

¹HNMR(CDCl₃) δ:
1.02 (6H, s), 1.03 (6H, s), 2.40 (4H, m),
2.51 (2H, m), 2.84 (1H, m), 3.24 (1H, m),
3.35 (1H, m), 3.42 (1H, m), 8.70 (1H, d),
9.08 (1H, d).

EXAMPLE 134

2-[(2-(2,2,6,6-tetramethylpiperidin-1-yl)methyl)sulfinyl]1H-imidazo[4,5-b]pyridine

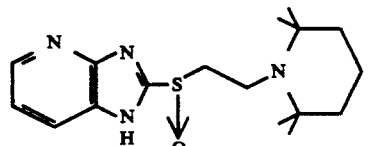

¹HNMR(CDCl₃) δ:
1.00 (12H, d), 1.34–1.39 (4H, m3),
1.47–1.50 (2H, m3), 2.80–2.88 (1H, m),
3.19–3.27 (1H, m), 3.31–3.40 (2H, m), 7.37 (1H, dd), 8.14 (1H, d), 8.74 (1H, d).
EI (m/z): 334 (M+)
335 (M+1)

EXAMPLE 135

2-[(carbamoylmethyl)sulfinyl]thiazolo[5,4-b]pyridine

¹HNMR(CDCl₃) δ:
4.15 (2H, ABq), 7.53 (1H, brs), 7.70 (1H, dd),
7.80 (1H, brs), 8.52 (1H, dd), 8.74 (1H, dd).

EXAMPLE 136

2-[(2-di-isopropylaminomethyl)sulfinyl]thiazolo[4,5-b]pyridine

¹HNMR(CDCl₃) δ:
1.03 (6H, d), 1.10 (6H, d), 2.98 (1H, m),
3.01–3.30 (4H, m), 3.51 (1H, m), 7.43 (1H, dd),
8.39 (1H, dd), 8.81 (1H, dd).

EXAMPLE 137

2-[(2-di-isopropylaminomethyl)sulfinyl)methyl]-thiazolo[5,4-b]pyridine

¹HNMR(CDCl₃) δ:
1.01 (6H, d), 1.04 (6H, d), 2.75–3.10 (6H, m),
4.41 (1H, d), 4.60 (1H, d), 7.46 (1H, dd).

EXAMPLE 138

2-[(2-morpholinomethyl)sulfinyl]thiazolo[5,4-b]pyridine

¹HNMR(CDCl₃) δ:
2.47 (4H, t), 2.84–3.00 (1H, m), 3.32–3.54 (3H, m),
7.54 (1H, dd), 8.28 (1H, d), 8.67 (1H, d).
EI (m/z): 297 (M+)

EXAMPLE 139

2-[(2-morpholinomethyl)sulfonyl]thiazolo[5,4-b]pyridine

¹HNMR(CDCl₃) δ:
2.35 (4H, s), 2.93 (2H, t), 3.17 (4H, s),
3.74 (2H, t), 7.61 (1H, dd), 8.45 (1H, dd),
8.80 (1H, d).
EI (m/z): 313 (M+)

EXAMPLE 140

2-[(2-morpholinomethyl)sulfinyl]thiazolo[4,5-c]pyridine

¹HNMR(CDCl₃) δ:
2.46 (4H, t), 2.86–3.00 (2H, m), 3.37–3.43 (6H, m),
7.98 (1H, d), 8.64 (1H, d), 9.34 (1H, s).
EI (m/z): 297 (M+)

EXAMPLE 141

2-[(2-N,N-diethylaminomethyl)sulfinyl]thiazolo[5,4-b]pyridine

¹HNMR(CDCl₃) δ:
1.00 (6H, t), 2.52–2.66 (4H, m), 2.87–2.94 (1H, m),
3.08–3.16 (1H, m), 3.24–3.33 (1H, m),
3.37–3.44 (1H, m), 7.52 (1H, dd), 8.28 (1H, d),
8.66 (1H, d).
EI (m/z): 283 (M+)

EXAMPLE 142

6-chloro-2
2-[(2-morpholinomethyl)sulfinyl]thiazolo[5,4-b]pyridine

¹HNMR(CDCl₃) δ:
2.46 (4H, t), 2.84–3.00 (2H, m), 3.32–3.44 (4H, m),
3.46–3.52 (2H, m), 8.26 (1H, d), 8.26 (1H, d),
8.64 (1H, d).

EI (m/z): 331 (M+)

EXAMPLE 143

2-[(2-morpholinoethyl)sulfinyl]imidazo[4,5-b]pyridine

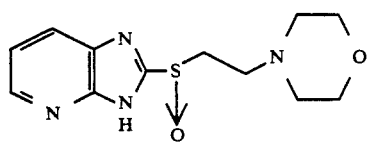

¹HNMR(CDCl₃) δ:
2.43 (4H, t), 2.92 (1H, m), 3.37 (2H, m),
3.43-3.55 (4H, m), 7.38 (1H, dd), 8.13 (1H, d),
8.76 (1H, d).
EI (m/z): 280 (M+)

EXAMPLE 144

2-[(2-(1-methylpyrrolidin-2-yl)ethyl)sulfinyl]-thiazolo[5,4-b]pyridine

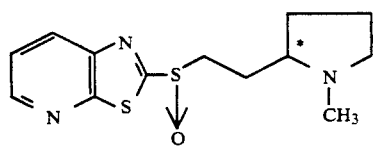

¹HNMR(CDCl₃) δ:
1.42-1.55 (1H, m), 1.61-1.77 (3H, m),
1.88-1.98 (1H, m), 1.98-2.07 (1H, m), 2.19 (1H, q),
2.30 (3H, d), 3.03-3.07 (1H, m), 3.13-3.21 (1H, m),
3.25-3.29 (1H, m), 3.32-3.41 (1H, m), 7.53 (1H, m),
8.31 (1H, d), 8.69 (1H, d).
EI (m/z): 295 (M+)

EXAMPLE 145

2-[(2-(1-methylpyrrolidin-2-yl)ethyl)sulfonyl]-thiazolo[5,4-b]pyridine

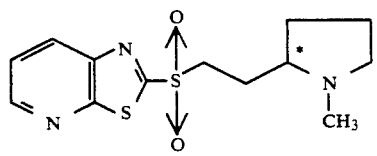

¹HNMR(CDCl₃) δ:
1.47 (1H, m), 1.72 (2H, m), 1.94 (2H, m),
2.16 (2H, m), 2.27 (3H, s), 2.30-2.36 (1H, m),
3.03 (1H, m), 3.47 (1H, m), 3.68 (1H, m),
7.62 (1H, dd), 8.47 (1H, d), 8.79 (1H, d).
EI (m/z): 311 (M+)

EXAMPLE 146

2-[(2-ureidoethyl)sulfinyl]thiazolo[5,4-b]pyridine

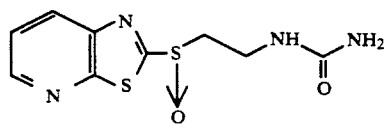

¹HNMR(CDCl₃) δ:
3.40-3.50 (4H, m), 7.72 (1H, dd), 8.52 (1H, d),
8.52 (1H, d), 8.73 (1H, d).

EI (m/z): 302 (M+)

EXAMPLE 147

2-[(1-methylpiperidin-3-yl)methylsulfinyl]thiazolo[5,4-b]pyridine

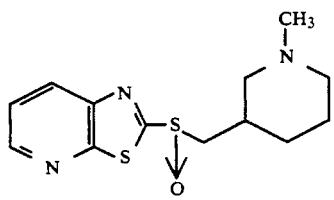

¹HNMR(CDCl₃) δ:
1.16-1.33 (1H, m), 1.58-1.61 (2H, m), 1.75 (2H, m),
1.83-1.93 (2H, m), 2.25 (3H, d), 2.36-2.48 (1H, m),
2.65 (1H, m), 2.93-2.83 (1H, dd), 3.12-3.19 (2H, m),
7.53 (1H, dd), 8.32 (1H, d), 8.68 (1H, d).
EI (m/z): 295 (M+)

EXAMPLE 148

2-[(1-methylpiperidin-4-yl)sulfinyl]thiazolo[5,4-b]pyridine

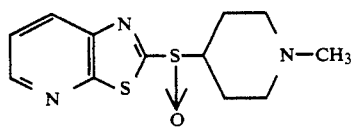

¹HNMR(CDCl₃) δ:
1.84-2.15 (6H, m), 2.27 (3H, d), 2.95-2.98 (2H, m),
3.07-3.13 (1H, m), 7.53 (1H, dd), 8.33 (1H, d),
8.68 (1H, d).
EI (m/z): 281 (M+)

EXAMPLE 149

2-[(2-di-isopropylaminoethyl)sulfinyl]thiazolo[5,4-b]pyridine

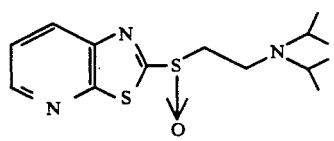

¹HNMR(CDCl₃) δ:
1.03 (6H, d), 1.08 (6H, d), 2.93-2.98 (1H, m),
3.04-3.14 (2H, m), 3.16-3.23 (2H, m),
3.32-3.40 (1H, m), 7.52 (1H, dd), 8.28 (1H, d),
8.67 (1H, d).
EI (m/z): 311 (M+)

EXAMPLE 150

2-[(2-di-isoopropylaminoethyl)sulfonyl]thiazolo[5,4-b]pyridine

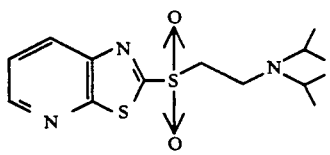

¹HNMR(CDCl₃) δ:
0.95 (12H, t), 2.96 (2H, m), 3.07 (2H, t),
3.63 (2H, t), 7.62 (1H, dd), 8.47 (1H, d),
8.79 (1H, d).
EI (m/z): 327 (M+)

EXAMPLE 151

2-[(3-(1-methylpiperazin-4-yl)propyl)sulfinyl]-thiazolo[5,4-b]pyridine

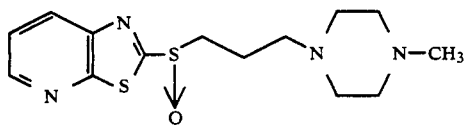

¹HNMR(CDCl₃) δ:
1.80-1.91 (1H, m), 2.12-2.23 (1H, m), 2.28 (3H, s),
2.39-2.56 (9H, m), 3.30 (3H, m), 7.53 (1H, dd),
8.31 (1H, d), 8.68 (1H, d).
EI (m/z): 324 (M+)

EXAMPLE 152

2-[(2-di-n-butylaminoethyl)sulfinyl]thiazolo[5,4-b]pyridine

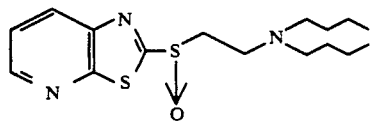

¹HNMR(CDCl₃) δ:
0.89 (6H, t), 1.27-1.35 (4H, m), 1.35-1.43 (4H, m),
2.43-2.50 (4H, m), 2.85-2.91 (1H, m),
3.11-3.18 (1H, m), 3.24-3.27 (1H, m),
3.38-3.45 (1H, m), 7.52 (1H, dd), 8.30 (1H, d),
8.67 (1H, d).
EI (m/z): 339 (M+)

EXAMPLE 153

Sodium (thiazolo[5,4-b]pyridin-2-yl)sulfinylacetate

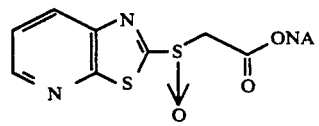

In ethanol, the compound set forth in Ex. 93 was hydrolyzed with 1N sodium hydroxide, and was purified by column chromatography (LH-20, Pharmacia Inc.) to obtain the title compound.

¹HNMR(CDCl₃) δ: 4.03 (2H, d), 7.50 (1H, dd), 8.10 (1H, d), 8.41 (1H, d).

EXAMPLE 154

(Pharmaceutical Composition)

|  |  | mg/tablet |
|---|---|---|
| (a) | Oral tablet |  |
|  | Compound of Example 79 | 15 |
|  | Lactose | 49.2 |
|  | Starch | 30 |
|  | Polyvinylpyrrolidone | 6 |
|  | Microcrystalline Cellulose | 18 |
|  | Colloidal Silica | 1.2 |
|  | Magnesium Stearate | 0.6 |
|  | Total | 120 |
| (b) | Oral Capsule |  |
|  | Compound of Example 79 | 25 |
|  | Lactose | 100 |
|  | Starch | 13 |
|  | TC-5 | 10 |
|  | Magnesium Stearate | 2 |
|  | Total | 150 |

EXAMPLE 155

(Pharmacological Data)

1. Water-immersion, restraint stress ulcerogenic testing

Wister male rats (11-week age) fasted for 18 hours were placed in a restraint cage, which was in turn immersed to a depth of the pectoral region in water at 20° to 22° C. to leave the rats under stress for six hours. Then, the rats were drawn up from the water and put down by vertebral dislocation. Afterwards, the stomach was removed, infused with 50 ml of a 5% aqueous solution of formalin and was wholly immersed in the same solution for 30 minutes for fixation. The fixed sample was dissected along the curvatura ventriculi major, and the ulcerated regions were measured along their major length (in mm) by means of slide calipers. The total sum of the measurements per rat is a value of ulceration. The compounds under test, suspended in 0.5% carboxymethylcellulose (CMC), were administered to the rats at a single dose of 5 ml/kg body weight (corresponding to 30 mg/kg body weight of the compound) one hour prior to the stressing. To a control group, only 0.5% CMC was administrated at a dose of 5 ml/kg weight. The rate of depression of ulceration was calculated according to the following equation:

$$\text{Percent Ulceration Inhibition} = \left(1 - \frac{\text{Average value of ulceration in the test group}}{\text{Average value of ulceration in the control group}}\right) \times 100$$

The results are set forth in Table 1.

2. Ethanol-induced ulceration

Five (5) ml/kg of 100% ethanol was orally administrated to Donryu masculine rats fasted for 48 hours and dehydrated for 24 hours. One hour later, the rats were put down in similar manners as mentioned above test to remove and treat the stomach. The compounds under test, suspended in 0.5% CMC, were orally administered to the rats at a dose of 5 ml/kg body weight (corresponding to 30 mg/kg body weight of that compound) one hour prior to the administration of ethanol. A control group, to which only 0.5% CMC was administered, showed a nearly 100% erosion, whereas the compound of Example 79, for instance, achieved a 98% depression of erosion. Effects of other compounds under test upon ulceration, determined in similar manners as mentioned above, are set forth in Table 2.

3. Toxicity

The compounds of the present invention are of low toxicity, as appreciated from Example Compound Nos. 79, 104 and 133 having up to 1 g/kg of $LD_{50}$ value (mice, by an oral).

TABLE 1

| Compound of Example No. | % Ulceration Inhibition |
|---|---|
| 47 | 99 |
| 48 | 99 |
| 51 | 88 |
| 65 | 58 |
| 70 | 42 |
| 79 | 76 |
| 84 | 75 |
| 89 | 72 |
| 93 | 73 |
| 100 | 95 |
| 101 | 75 |
| 103 | 84 |
| 104 | 68 |
| 110 | 79 |
| 117 | 77 |
| 120 | 86 |
| 121 | 67 |
| 122 | 13 |
| 123 | 15 |
| 124 | 25 |
| 125 | 44 |
| 126 | 60 |
| 127 | 0 |
| 128 | 91 |
| 129 | 99 |
| 130 | 76 |
| 131 | 71 |
| 133 | 98 |
| 135 | 86 |
| 136 | 94 |
| 138 | 68 |
| 139 | 47 |
| 140 | 58 |
| 141 | 41 |
| 142 | 13 |
| 143 | 54 |
| 144 | 85 |
| 145 | 68 |
| 146 | 19 |
| 147 | 64 |
| 148 | 78 |
| 149 | 99 |
| 150 | 61 |
| 151 | 39 |

TABLE 2

| Compound of Example No. | % Ulceration Inhibition |
|---|---|
| 79 | 98 |
| 128 | 99 |
| 138 | 97 |
| 149 | 94 |

What is claimed is:

1. A compound of the formula

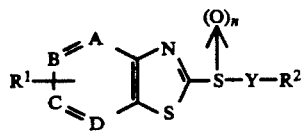

wherein
one of A, B, C and D represents —N= and the others represent —CH=;
Y represents (CH$_2$)$_p$ wherein p is an integer of 1-4;
$R^1$ represents (1) a hydrogen atom, (2) a $C_{1-4}$ alkyl group which is unsubstituted or substituted by fluorine (3) a halogen atom, (4) a $C_{1-4}$ alkoxy group, (5) methoxymethyl, (6)) ethoxymethyl, or (7) 2,2,2-trifluoroethoxy
$R^2$ represents a five or six membered heterocyclic group containing at least one nitrogen atom which may be either saturated or unsaturated, may be substituted by a substituent and may be condensed with another ring and selected from the group consisting of 1-pyrrolidinyl, 2-pyrrolidinyl, 3-pyrrolidinyl, 2-(1-methyl)pyrrolidinyl, 3-(1-methyl)-pyrrolidinyl, 2-(1-ethyl)pyrrolidinyl, 3-(1-ethyl) pyrrolidinyl, 1-piperazinyl, 1-(4-methyl)piperazinyl, 1-piperidinyl, 2-(1-methyl)piperidinyl, 3-(1-methyl)piperidinyl, 4-(1-methyl) piperidinyl, 2,6-dimethyl-1-piperidinyl, 2,2,6,6-tetramethyl-1-piperidinyl, 2-pyridinyl, 3-pyridinyl, 4-pyridinyl, 2-oxazolidinon-5-yl, morpholinyl, 1-methyltetrazol-5-yl, 1-cyclohexyltetrazol-5-yl, 1,3-dioxisoindol-2-yl, and 4-methylimidazol-5-yl, and
n is an integer from 0 and 2,
or a pharmaceutically acceptable salt thereof.

2. A compound as claimed in claim 1 selected from the group consisting of 2-[(2-morpholinoethyl)sulfinyl]-thiazolo[5,4-b]pyridine; 2-[(4-(1-methyltetrazol-5-yl)butyl)sulfonyl]thiazolo[5,4-b]pyridine;
2-[(2-(2,2,6,6-tetramethylpiperidin-1-yl)ethyl)sulfinyl]-thiazolo[5,4-b]pyridine; and
2-[2-(2,2,6,6-tetramethylpiperidin-1-yl)ethylthio]-6-trifluoromethylthiazolo[4,5-b]pyridine.

3. A compound according to claim 1 said compound being 2-[2,2,6,6-tetramethylpiperidin-1-yl)ethylthio]-6-trifluoromethylthiazolo[4,5-b]pyridine.

4. A pharmaceutical composition comprising a pharmaceutically effective amount of a compound as claimed in claim 1 and a pharmaceutically acceptable carrier therefor.

5. A pharmaceutical composition comprising a pharmaceutically effective amount of a compound as claimed in claim 2 and a pharmaceutically acceptable carrier therefor.

* * * * *